(12) United States Patent
Eisen et al.

(10) Patent No.: US 12,083,025 B2
(45) Date of Patent: Sep. 10, 2024

(54) INTERVERTEBRAL CAGES WITH INTEGRATED EXPANSION AND ANGULAR ADJUSTMENT MECHANISM

(71) Applicant: EIT Emerging Implant Technologies GmbH, Wurmlingen (DE)

(72) Inventors: Guntmar Eisen, Wurmlingen (DE); Detlev Ganter, Wurmlingen (DE); Stephan Geiger, Wurmlingen (DE)

(73) Assignee: EIT Emerging Implant Technologies GmbH, Wurmlingen (DE)

( * ) Notice: Subject to any disclaimer, the term of this patent is extended or adjusted under 35 U.S.C. 154(b) by 19 days.

(21) Appl. No.: 17/103,995

(22) Filed: Nov. 25, 2020

(65) Prior Publication Data

US 2021/0077272 A1 Mar. 18, 2021

Related U.S. Application Data

(63) Continuation of application No. 16/293,483, filed on Mar. 5, 2019, now Pat. No. 10,869,769.
(Continued)

(51) Int. Cl.
*A61F 2/44* (2006.01)
*A61F 2/46* (2006.01)
(Continued)

(52) U.S. Cl.
CPC ............ *A61F 2/447* (2013.01); *A61F 2/4455* (2013.01); *A61F 2/4611* (2013.01);
(Continued)

(58) Field of Classification Search
None
See application file for complete search history.

(56) References Cited

U.S. PATENT DOCUMENTS

| 6,176,882 B1 | 1/2001 | Biedermann et al. |
| 9,532,883 B2 | 1/2017 | Mcluen et al. |
| (Continued) | | |

FOREIGN PATENT DOCUMENTS

| CN | 104023674 A | 9/2014 |
| CN | 205107983 U | 3/2016 |
| (Continued) | | |

*Primary Examiner* — Jan Christopher L Merene
(74) *Attorney, Agent, or Firm* — BakerHostetler

(57) ABSTRACT

The embodiments provide various interbody fusion spacers, or cages, for insertion between adjacent vertebrae. The cages may have integrated expansion and angular adjustment mechanisms that allow the cage to change its height and angle as needed, with little effort. The cages may have a first, insertion configuration characterized by a reduced size to facilitate insertion through a narrow access passage and into the intervertebral space. The cages may be inserted in a first, reduced size and then expanded to a second, larger size once implanted. In their second configuration, the cages are able to maintain the proper disc height and stabilize the spine by restoring sagittal balance and alignment. Additionally, the intervertebral cages are configured to be able to adjust the angle of lordosis, and can accommodate larger lordotic angles in their second, expanded configuration. Further, these cages may promote fusion to further enhance spine stability by immobilizing the adjacent vertebral bodies.

17 Claims, 21 Drawing Sheets

Related U.S. Application Data

(60) Provisional application No. 62/639,138, filed on Mar. 6, 2018.

(51) Int. Cl.
    *A61B 17/88*     (2006.01)
    *A61F 2/30*     (2006.01)

(52) U.S. Cl.
    CPC . *A61B 17/8858* (2013.01); *A61F 2002/30136* (2013.01); *A61F 2002/30143* (2013.01); *A61F 2002/30261* (2013.01); *A61F 2002/30266* (2013.01); *A61F 2002/30329* (2013.01); *A61F 2002/30331* (2013.01); *A61F 2002/30405* (2013.01); *A61F 2002/30411* (2013.01); *A61F 2002/30471* (2013.01); *A61F 2002/30507* (2013.01); *A61F 2002/30537* (2013.01); *A61F 2002/30538* (2013.01); *A61F 2002/3054* (2013.01); *A61F 2002/30556* (2013.01); *A61F 2002/30579* (2013.01); *A61F 2002/30622* (2013.01); *A61F 2002/30784* (2013.01); *A61F 2002/30787* (2013.01); *A61F 2002/3093* (2013.01); *A61F 2002/443* (2013.01); *A61F 2002/4627* (2013.01)

(56) References Cited

U.S. PATENT DOCUMENTS

| | | | |
|---|---|---|---|
| 9,750,618 | B1 | 9/2017 | Daffinson et al. |
| 9,839,527 | B2* | 12/2017 | Robinson ................ A61F 2/447 |
| 10,052,215 | B2 | 8/2018 | Hessler et al. |
| 10,856,997 | B2* | 12/2020 | Cowan ................... A61F 2/447 |
| 11,419,735 | B2* | 8/2022 | Barreiro ................ A61F 2/4611 |
| 2004/0254644 | A1* | 12/2004 | Taylor ................... A61F 2/4425 623/17.13 |
| 2005/0125061 | A1 | 6/2005 | Zucherman et al. |
| 2006/0206207 | A1* | 9/2006 | Dryer ..................... A61F 2/446 606/104 |
| 2007/0270968 | A1* | 11/2007 | Baynham ................ A61F 2/447 623/17.11 |
| 2008/0140207 | A1* | 6/2008 | Olmos ................... A61F 2/4611 623/17.11 |
| 2009/0216331 | A1 | 8/2009 | Grotz et al. |
| 2013/0158663 | A1 | 6/2013 | Miller et al. |
| 2013/0158664 | A1* | 6/2013 | Palmatier ............. A61F 2/4425 623/17.16 |
| 2014/0236296 | A1 | 8/2014 | Wagner et al. |
| 2014/0243982 | A1 | 8/2014 | Miller |
| 2014/0257486 | A1* | 9/2014 | Alheidt ................. A61F 2/4455 623/17.15 |
| 2015/0351925 | A1 | 12/2015 | Emerick et al. |
| 2016/0120660 | A1 | 5/2016 | Melkent et al. |
| 2017/0296352 | A1* | 10/2017 | Richerme ............. A61F 2/4425 |
| 2017/0367845 | A1 | 12/2017 | Eisen et al. |
| 2018/0036138 | A1* | 2/2018 | Robinson ............... A61F 2/4611 |
| 2018/0147065 | A1 | 5/2018 | Daffinson et al. |
| 2019/0021873 | A1* | 1/2019 | Dmuschewsky ..... A61F 2/4425 |

FOREIGN PATENT DOCUMENTS

| | | | |
|---|---|---|---|
| CN | 105640675 | A | 6/2016 |
| CN | 106264805 | A | 1/2017 |
| CN | 106726020 | A | 5/2017 |
| CN | 107106305 | A | 8/2017 |
| CN | 107224341 | A | 10/2017 |
| CN | 107569307 | A | 1/2018 |
| EP | 2992859 | A1 | 3/2016 |
| WO | 99/42062 | A1 | 8/1999 |
| WO | 2017/101989 | A1 * | 6/2018 ............ A61F 2/442 |

* cited by examiner

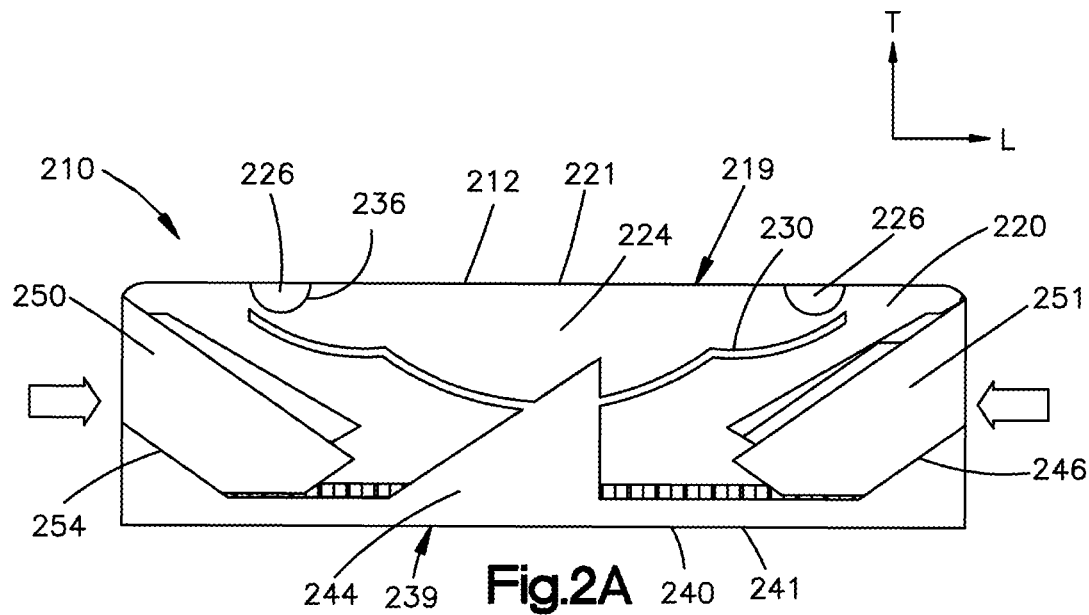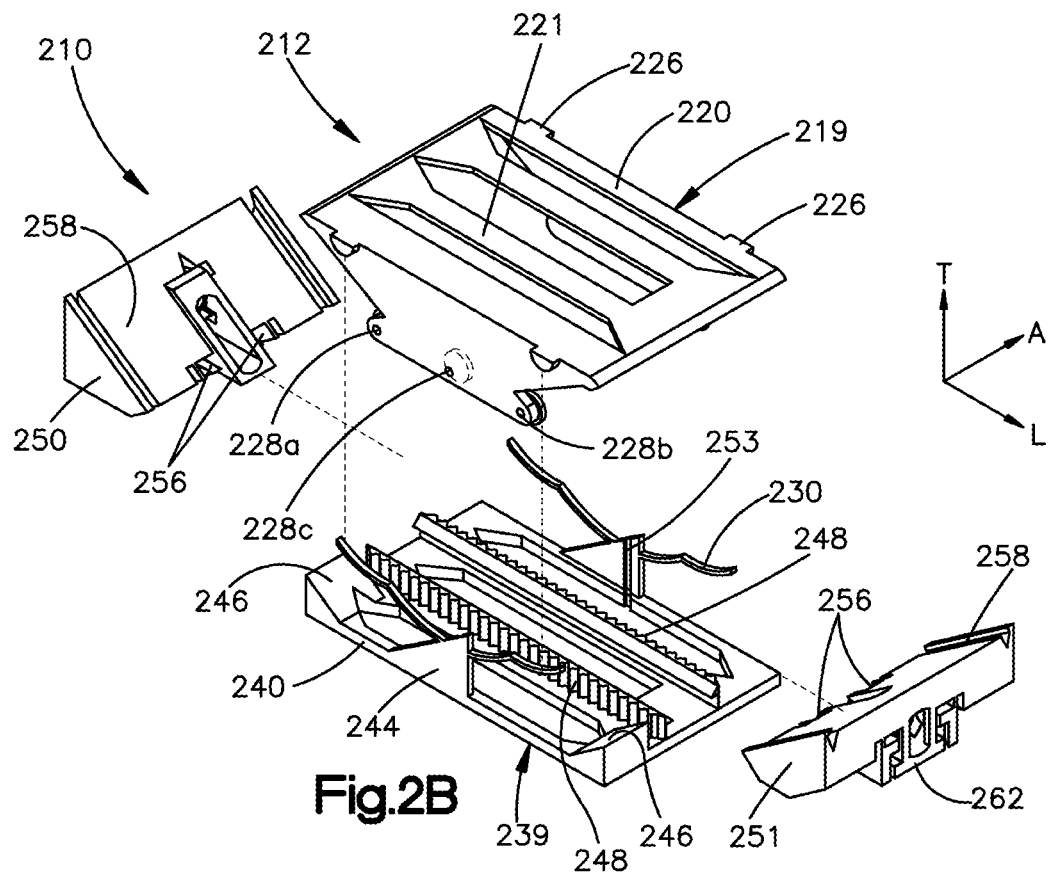

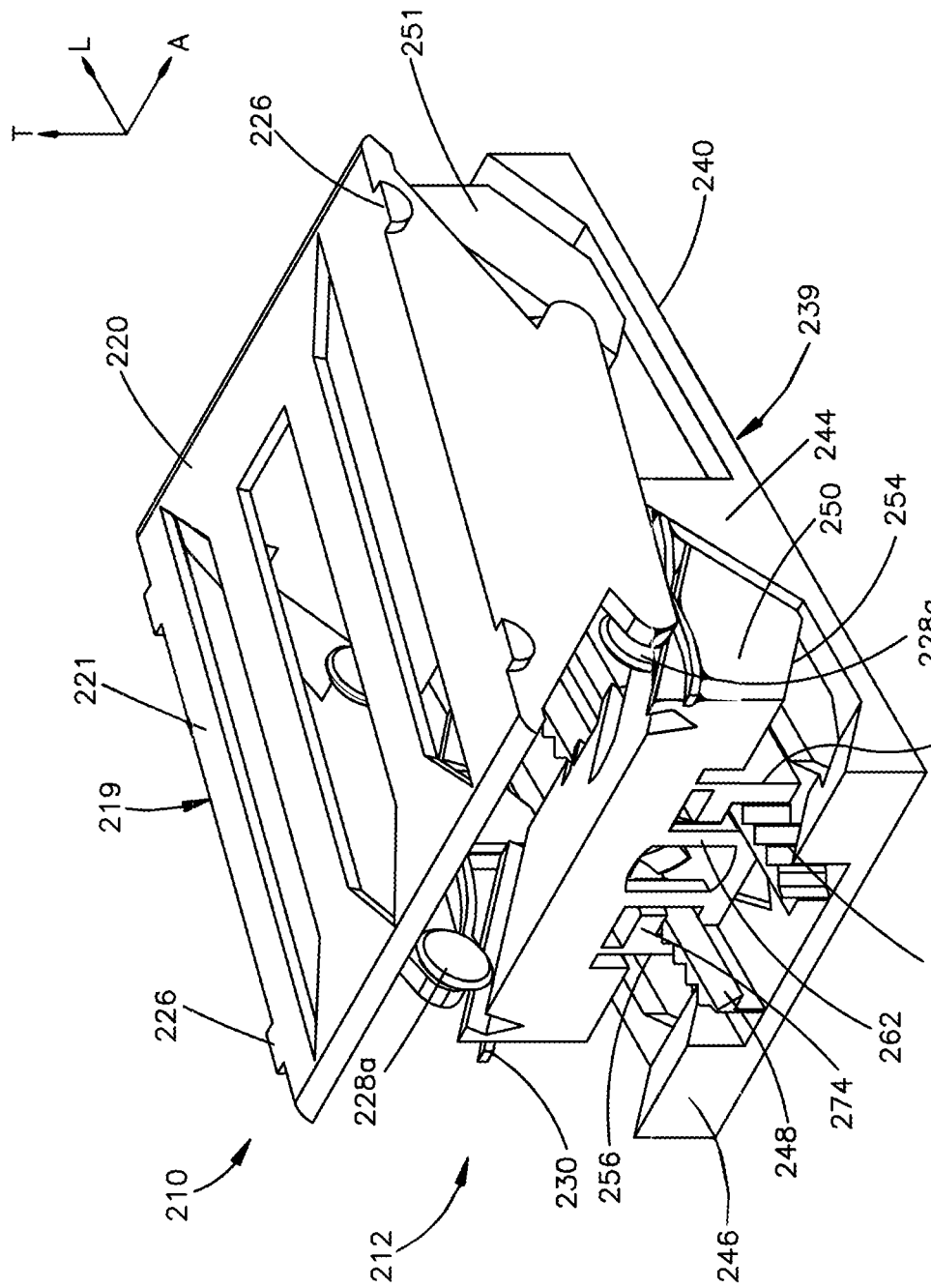

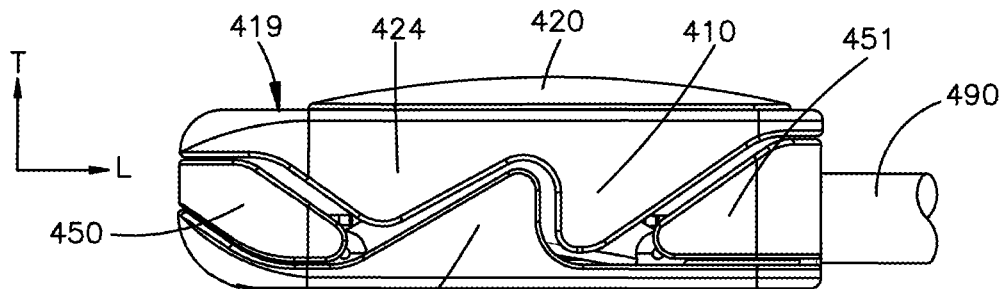
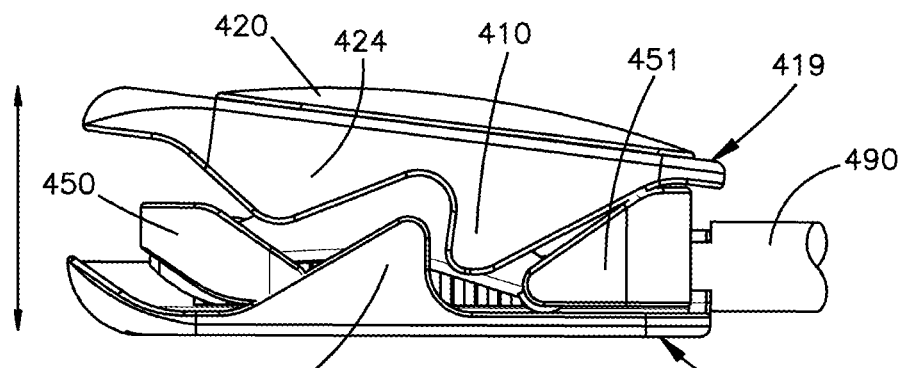
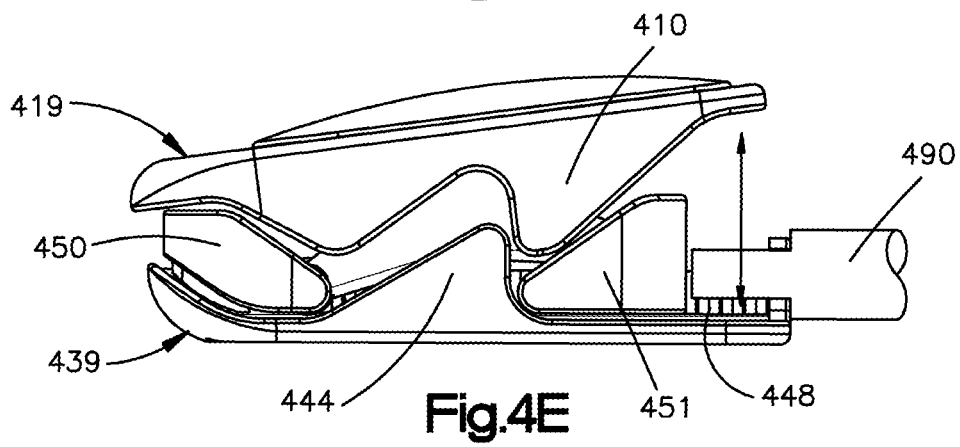
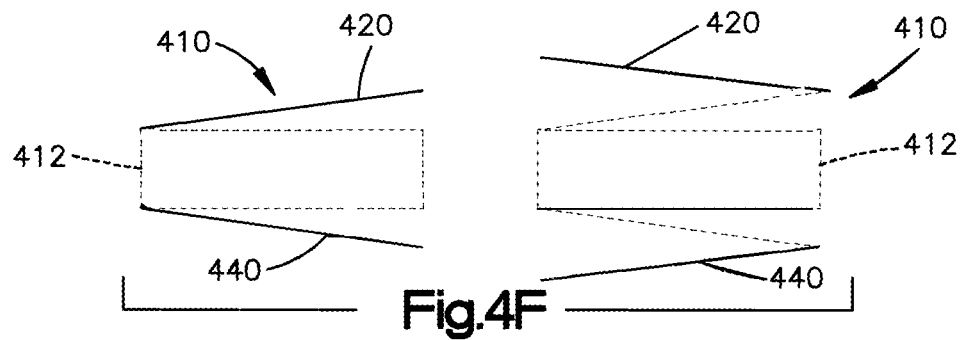

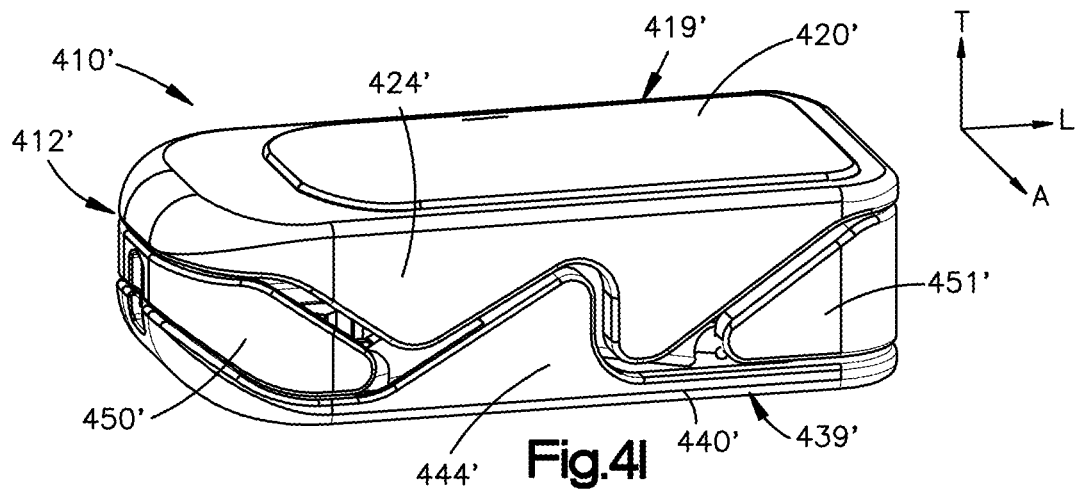
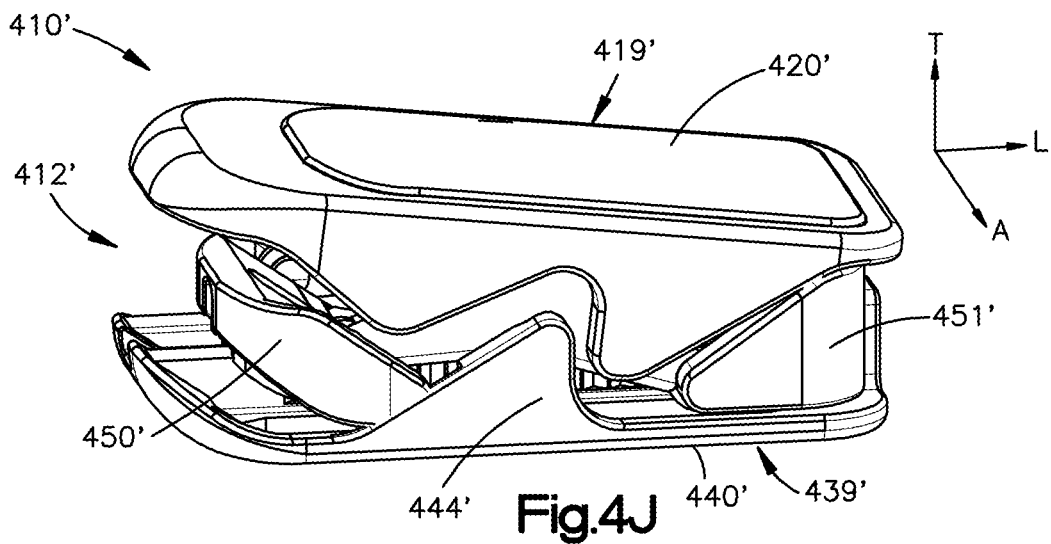
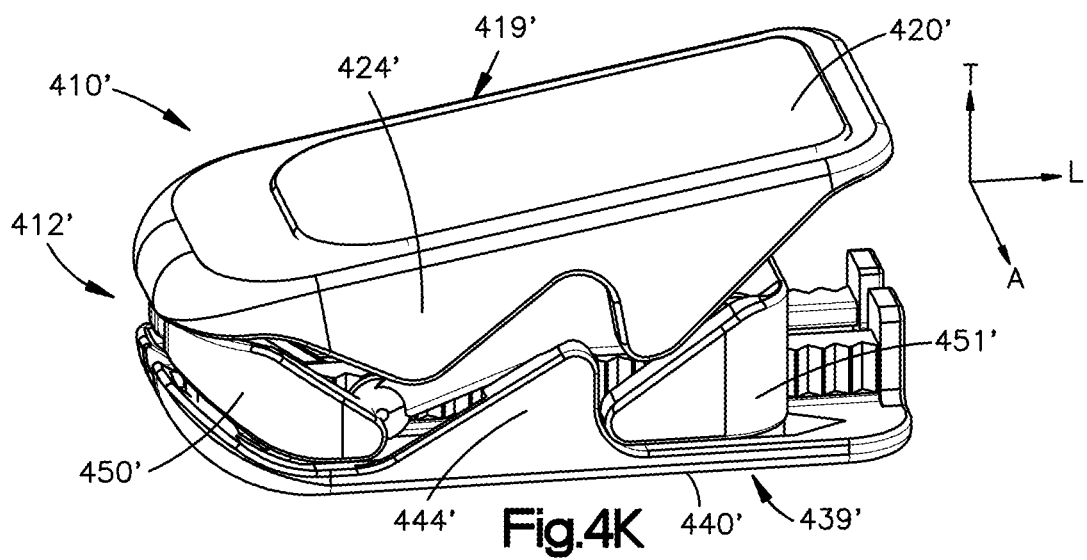

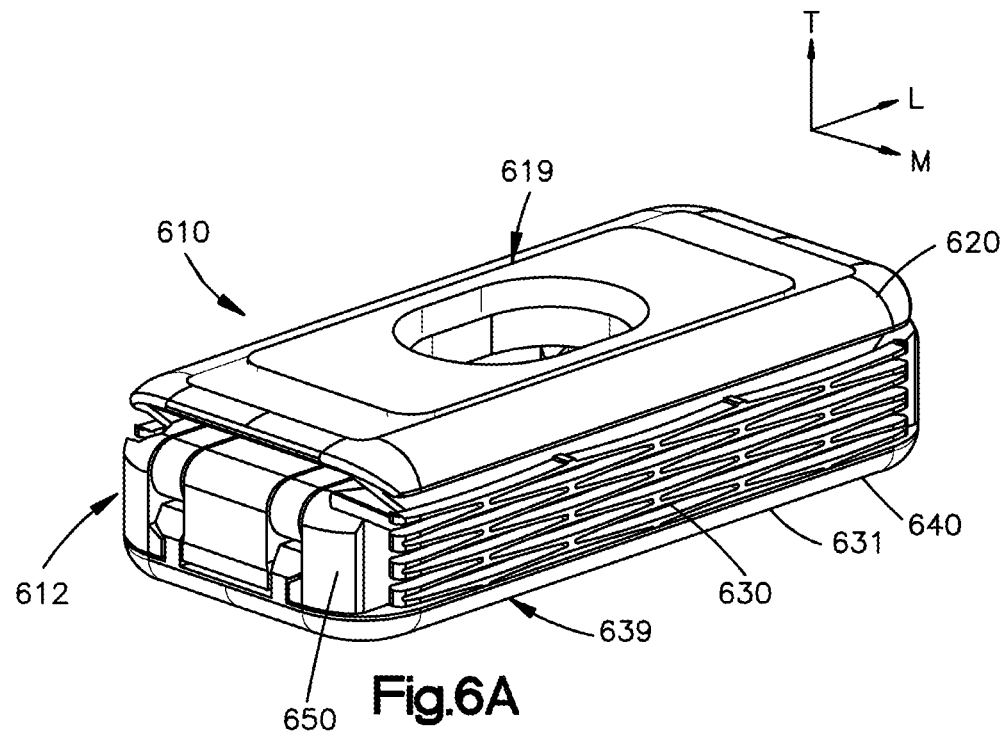
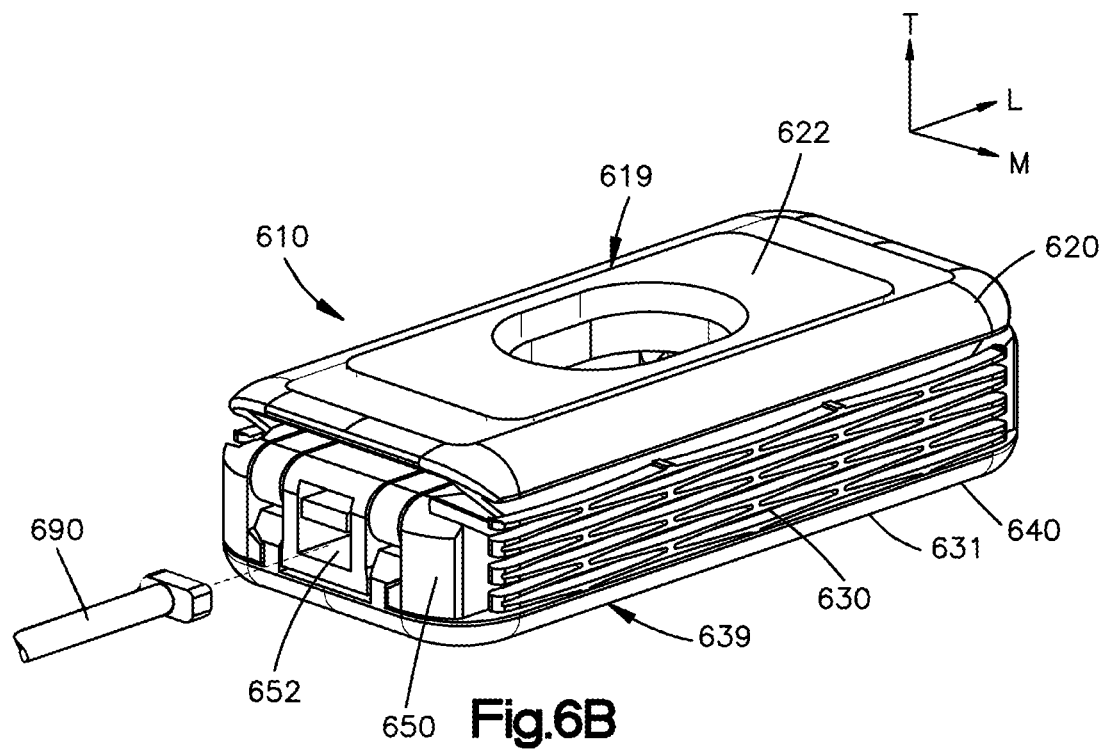

INTERVERTEBRAL CAGES WITH INTEGRATED EXPANSION AND ANGULAR ADJUSTMENT MECHANISM

CROSS-REFERENCE TO RELATED APPLICATIONS

This is a continuation of U.S. patent application Ser. No. 16/293,483 filed Mar. 5, 2019, which claims the benefit of U.S. Patent Application Ser. No. 62/639,138 filed Mar. 6, 2018, the disclosure of which is hereby incorporated by reference as if set forth in its entirety herein.

TECHNICAL FIELD

The present disclosure relates to implantable orthopedic devices, and more particularly to implantable devices for stabilizing the spine. Even more particularly, the present disclosure relates to intervertebral cages comprising integrated expansion and angular adjustment mechanisms that allow expansion of the cages from a first, insertion configuration having a reduced size to a second, implanted configuration having an expanded size. The intervertebral cages are able to adjust angularly, and adapt to lordotic angles, particularly larger lordotic angles, while restoring sagittal balance and alignment of the spine.

BACKGROUND

The use of fusion-promoting interbody implantable devices, often referred to as cages or spacers, is well known as the standard of care for the treatment of certain spinal disorders or diseases. For example, in one type of spinal disorder, the intervertebral disc has deteriorated or become damaged due to acute injury or trauma, disc disease or simply the natural aging process. A healthy intervertebral disc serves to stabilize the spine and distribute forces between vertebrae, as well as cushion the vertebral bodies. A weakened or damaged disc therefore results in an imbalance of forces and instability of the spine, resulting in discomfort and pain. The standard treatment today may involve surgical removal of a portion, or all, of the diseased or damaged intervertebral disc in a process known as a partial or total discectomy, respectively. The discectomy is often followed by the insertion of a cage or spacer to stabilize this weakened or damaged spinal region. This cage or spacer serves to reduce or inhibit mobility in the treated area, in order to avoid further progression of the damage and/or to reduce or alleviate pain caused by the damage or injury. Moreover, these types of cages or spacers serve as mechanical or structural scaffolds to restore and maintain normal disc height, and in some cases, can also promote bony fusion between the adjacent vertebrae.

However, one of the current challenges of these types of procedures is the very limited working space afforded the surgeon to manipulate and insert the cage into the intervertebral area to be treated. Access to the intervertebral space requires navigation around retracted adjacent vessels and tissues such as the aorta, vena cava, dura and nerve roots, leaving a very narrow pathway for access. The opening to the intradiscal space itself is also relatively small. Hence, there are physical limitations on the actual size of the cage that can be inserted without significantly disrupting the surrounding tissue or the vertebral bodies themselves.

Further complicating the issue is the fact that the vertebral bodies are not positioned parallel to one another in a normal spine. There is a natural curvature to the spine due to the angular relationship of the vertebral bodies relative to one another. The ideal cage must be able to accommodate this angular relationship of the vertebral bodies, or else the cage will not sit properly when inside the intervertebral space. An improperly fitted cage would either become dislodged or migrate out of position, and lose effectiveness over time, or worse, further damage the already weakened area.

Thus, it is desirable to provide intervertebral cages or spacers that not only have the mechanical strength or structural integrity to restore disc height or vertebral alignment to the spinal segment to be treated, but also be configured to easily pass through the narrow access pathway into the intervertebral space, and then accommodate the angular constraints of this space, particularly for larger lordotic angles.

BRIEF SUMMARY

The present disclosure describes spinal implantable devices that address the aforementioned challenges and meet the desired objectives. These spinal implantable devices, or more specifically intervertebral cages or spacers, are configured to be expandable as well as angularly adjustable. The cages may comprise upper and lower plates for bearing against endplates of the vertebral bodies, and have integrated expansion and angular adjustment mechanisms that allow the cage to change size and angle as needed, with little effort. In some embodiments, the cages may have a first, insertion configuration characterized by a reduced insertion size to facilitate insertion through a narrow access passage and into the intervertebral space. The cages may be inserted in the first configuration and once the cage is implanted, the cage can be expanded to a second configuration having a larger size than the insertion size. In their second configuration, the cages are able to maintain the proper disc height and stabilize the spine by restoring sagittal balance and alignment. Additionally, the intervertebral cages are configured to be able to adjust the angle of lordosis, and can accommodate larger lordotic angles, as well as provide pure expansion only (i.e., height adjustment), or a combination of both angular and height adjustment, in their second, expanded configuration. Further, these cages may promote fusion to further enhance spine stability by immobilizing the adjacent vertebral bodies.

According to one aspect of the disclosure, the cages may be manufactured using selective laser melting (SLM) techniques, a form of additive manufacturing. The cages may also be manufactured by other comparable techniques, such as for example, 3D printing, electron beam melting (EBM), layer deposition, and rapid manufacturing. With these production techniques, it is possible to create an all-in-one, multi-component device which may have interconnected and movable parts without further need for external fixation or attachment elements to keep the components together. Accordingly, the intervertebral cages of the present disclosure are formed of multiple, interconnected parts that do not require additional external fixation elements to keep together.

Even more relevant, cages manufactured in this manner would not have connection seams whereas devices traditionally manufactured would have joined seams to connect one component to another. These connection seams can often represent weakened areas of the implantable device, particularly when the bonds of these seams wear or break over time with repeated use or under stress. By manufacturing the disclosed implantable devices using additive manufacturing, one of the advantages is that connection seams are avoided entirely and therefore the problem is avoided.

Another advantage of the present devices is that, by manufacturing these devices using an additive manufacturing process, all of the components of the device remain a complete construct during both the insertion process as well as the expansion process. That is, multiple components are provided together as a collective single unit so that the collective single unit is inserted into the patient, actuated to allow expansion, and then allowed to remain as a collective single unit in situ. In contrast to other cages requiring insertion of external screws or wedges for expansion, in the present embodiments the expansion and blocking components do not need to be inserted into the cage, nor removed from the cage, at any stage during the process. This is because these components are manufactured so as to be captured internally within the cages, and while freely movable within the cage, are already contained within the cage so that no additional insertion or removal is necessary.

In some embodiments, the cages can have an engineered cellular structure on a portion of, or over the entirety of, the cage. This cellular structure can include a network of pores, microstructures and nanostructures to facilitate osteosynthesis. For example, the engineered cellular structure can comprise an interconnected network of pores and other micro and nano sized structures that take on a mesh-like appearance. These engineered cellular structures can be provided by etching or blasting, to change the surface of the device on the nano level. One type of etching process may utilize, for example, HF acid treatment.

In addition, these cages can also include internal imaging markers that allow the user to properly align the device and generally facilitate insertion through visualization during navigation. The imaging marker shows up as a solid body amongst the mesh under x-ray, fluoroscopy or CT scan, for example.

Another benefit provided by the implantable devices of the present disclosure is that they can be specifically customized to the patient's needs. Customization of the implantable devices is relevant to providing a preferred modulus matching between the implant device and the various qualities and types of bone being treated, such as for example, cortical versus cancellous, apophyseal versus central, and sclerotic versus osteopenic bone, each of which has its own different compression to structural failure data. Likewise, similar data can also be generated for various implant designs, such as for example, porous versus solid, trabecular versus non-trabecular, etc. Such data may be cadaveric, or computer finite element generated. Clinical correlation with, for example, DEXA data can also allow implantable devices to be designed specifically for use with sclerotic, normal, or osteopenic bone. Thus, the ability to provide customized implantable devices such as the ones provided herein allow the matching of the Elastic Modulus of Complex Structures (EMOCS), which enable implantable devices to be engineered to minimize mismatch, mitigate subsidence and optimize healing, thereby providing better clinical outcomes.

In one exemplary embodiment, an expandable spinal implant is provided. The expandable spinal implant may comprise a housing comprising an upper housing portion and a lower housing portion. The upper housing portion can include an upper plate configured for placement against an endplate of a first vertebral body. The lower housing portion can include a lower plate configured for placement against an endplate of a second, adjacent vertebral body. The upper housing portion can further include upper sidewalls that extend from the upper plate. The lower housing portion can include lower sidewalls that extend from the lower plate. The upper and lower sidewalls may be configured to slide along one another.

The expandable spinal implant may further include an expansion and angular adjustment mechanism within the housing that is configured to effect angular adjustment, height adjustment, or a combination of both, of the spinal implant. The expansion and angular adjustment mechanism may comprise a pair of wedges located at opposite ends of the housing, each wedge having a bearing surface for urging against the sidewalls of the upper and lower plates. In addition, the expansion and angular adjustment mechanism may further include a driver component connecting the wedges together and being configured to pull the wedges towards one another upon actuation.

Each of the upper and lower sidewalls may have a sloped profile. The housing may further include one or more deformable strips for controlling expansion of the intervertebral cage. The bearing surfaces of the wedges may comprise convex surfaces. The wedges may include a central opening for receiving the driver component therethrough. The driver component may include a tool-engaging member configured to couple to a tool to actuate the driver component. For instance, the driver can include an opening for receiving the tool to actuate the driver component. The expansion and angular adjustment mechanism is intended to be freely held within the housing.

In another exemplary embodiment, an expandable spinal implant is provided. The expandable spinal implant may comprise a housing comprising an upper plate configured for placement against an endplate of a first vertebral body, the upper plate having upper sidewalls extending therefrom, and a lower plate configured for placement against an endplate of a second, adjacent vertebral body, the lower plate having lower sidewalls extending therefrom.

The expandable spinal implant may further include an expansion and angular adjustment mechanism within the housing and be configured to effect angular adjustment, height adjustment, or a combination of both, of the spinal implant. The expansion and angular adjustment mechanism may comprise a pair of wedges located at opposite ends of the housing. Each wedge may have slots on a lower surface for translation along guide rails on the lower plate, such that movement of the wedges causes distraction or angulation of the plates relative to one another.

The wedges may have slots that are configured to receive projections of the upper housing portion to urge the upper plate away from the lower plate. The lower plate may further include elastically deformable strips extending from the lower sidewalls. The bearing surfaces of the wedges may comprise angled surfaces. The wedges may each include a tool-engaging opening. The upper plate may comprise rounded pins for engaging the elastically deformable strips of the lower plate, and further include rounded protrusions on an interior of the sidewalls, the rounded protrusions engaging the slots on the upper surface of the wedges. The slots on the upper surface of the wedges may be angled.

According to one aspect of the exemplary embodiment, the expandable spinal implant may comprise a porous structure located on the upper plate. According to another aspect, the porous structure may be located on the lower plate. In some embodiments, an elastically deformable screen may be provided extending between the upper and lower plates. In addition, teeth may be provided on the lower plate for enhanced anchorage to bone.

In some embodiments, the guide rails may comprise teeth. The wedges may further include click fingers for engaging the teeth of the guide rails. The wedges may be independently movable relative to one another, such that movement of one of the wedges effects angular displacement of the upper plate.

In yet another exemplary embodiment, an expandable spinal implant is provided. The expandable spinal implant may comprise a housing comprising an upper plate configured for placement against an endplate of a first vertebral body, and a lower plate configured for placement against an endplate of a second, adjacent vertebral body. The upper housing portion and lower housing portion may each have sidewalls that extend from the upper plate and lower plate, respectively, with each of the sidewalls including a set of projections, such as knobs. The housing may further include a set of brackets. Each bracket may be affixed to an actuator rod that extends out of an end of the housing. The housing may further include a vertical slot that is configured to receive a projection from each of the upper and lower plates. The projections of the sidewalls may reside within angled slots of the bracket. In use, pulling one of the rods effects movement of the knobs relative to the angled slots, which causes angular adjustment of the plates relative to the housing.

According to an aspect of the present disclosure, each of the sidewalls may include a set of projections that can be configured as knobs. Each of the actuator rods may be configured to horizontally translate in one direction only. The housing may include a top opening to allow the upper plate to extend out of the housing upon expansion, and a bottom opening to allow the lower plate to extend out of the housing upon expansion. The rods can be configured to be independently movable. Additionally, each bracket comprises a pair of angled slots, the angled slots being angled away from one another.

Although the following discussion focuses on spinal implants, it will be appreciated that many of the principles may equally be applied to other structural body parts requiring bone repair or bone fusion within a human or animal body, including other joints such as knee, shoulder, ankle or finger joints.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 2A is a lateral view of an intervertebral cage constructed in another example, showing the intervertebral cage in an insertion configuration;

FIG. 2B is an exploded perspective view of the intervertebral cage illustrated in FIG. 2A;

FIG. 2G is a perspective view of the intervertebral cage illustrated in FIG. 2F in an angularly adjusted configuration;

FIG. 4C is a side elevation view of the intervertebral cage illustrated in FIG. 4A, showing the cage in the insertion configuration;

FIG. 4D is a side elevation view of the intervertebral cage illustrated in FIG. 4C, but showing the cage in a first angularly adjusted configuration;

FIG. 4E is a side elevation view of the intervertebral cage illustrated in FIG. 4D, showing the cage in a second angularly adjusted configuration opposite the first angularly adjusted configuration;

FIG. 4F illustrates a principle of the angular adjustment of the intervertebral cage of FIG. 4A;

FIG. 4I is another perspective view of the intervertebral cage illustrated in FIG. 4G, shown in an initial configuration;

FIG. 4J is a perspective view of the intervertebral cage illustrated in FIG. 4I, but showing the cage in a first angularly adjusted configuration;

FIG. 4K is a perspective view of the intervertebral cage illustrated in FIG. 4J, but showing the cage in a second angularly adjusted configuration opposite the first angularly adjusted configuration;

FIG. 6A is a top perspective rear view of an intervertebral cage constructed in accordance with another example, shown in an initial or insertion configuration;

FIG. 6B is a perspective view of an implant assembly including the intervertebral cage illustrated in FIG. 6A and an associated actuator tool;

DETAILED DESCRIPTION

Figure 1A:
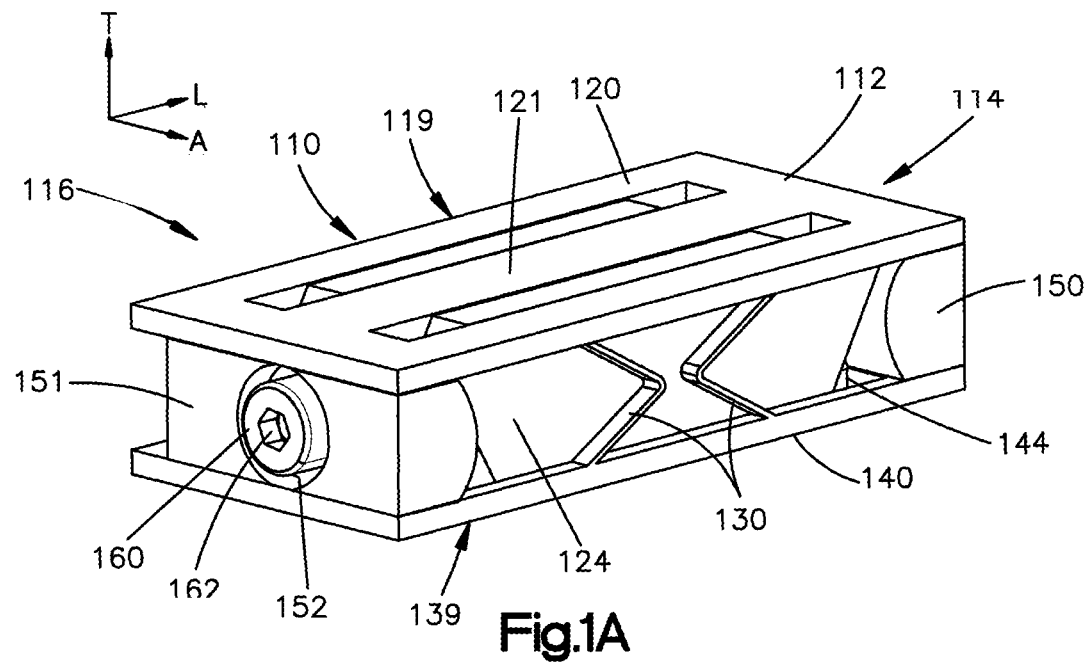
FIG. 1A is a perspective view of an intervertebral cage constructed in accordance with one example, shown in an insertion configuration.

The present disclosure provides various spinal implant devices, such as interbody fusion spacers, or cages, for insertion between adjacent vertebrae. The devices can be configured for use in either the cervical or lumbar region of the spine. In some embodiments, these devices may be configured as ALIF cages, or LLIF cages. However, it is contemplated that the principles of this disclosure may be equally utilized in transforaminal lumbar interbody fusion (TLIF) devices, posterior lumbar interbody fusion (PLIF) cages, and oblique lumbar interbody fusion (OLIF) cages.

These cages can restore and maintain intervertebral height of the spinal segment to be treated, and stabilize the spine by restoring sagittal balance and alignment. In some embodiments, the cages may have integrated expansion and angular adjustment mechanisms that allow the cage to change height and angle as needed, with little effort. The cages may have a first, insertion configuration characterized by a first or reduced size or height to facilitate insertion through a narrow access passage and into the intervertebral space. In some examples, the first or reduced height can define the minimum height achievable by the cages. The cages may be inserted in the first, insertion configuration, and then expanded to a second, expanded configuration once implanted. The second, expanded configuration can be characterized by a second or increased size or height that is greater than the first or reduced size or height. In their second configuration, the cages are able to maintain the proper disc height and stabilize the spine by restoring sagittal balance and alignment. Additionally, the plates of the intervertebral cages that contact the vertebral endplates are angularly adjustable. Thus, the intervertebral cages configured to be able to adjust the angle of lordosis or kyphosis, and can accommodate larger lordotic or kyphotic angles in their second, expanded configuration. In this regard, reference to lordotic angles when the cages are configured for implantation into the lumbar region of the spine can equally apply to kyphotic angles when the cages are configured for implantation into the cervical region of the spine. Further, these cages may promote fusion to further enhance spine stability by immobilizing the adjacent vertebral bodies.

Additionally, the implantable devices may be manufactured using selective laser melting (SLM) techniques, a form of additive manufacturing. The devices may also be manufactured by other comparable techniques, such as for example, 3D printing, electron beam melting (EBM), layer deposition, and rapid manufacturing. With these production techniques, it is possible to create an all-in-one, multi-component device which may have interconnected and movable parts without further need for external fixation or attachment elements to keep the components together. Accordingly, the intervertebral cages of the present disclosure are formed of multiple, interconnected parts that do not require additional external fixation elements to keep together.

Thus, devices manufactured in this manner would not have connection seams whereas devices traditionally manufactured would have joined seams to connect one component to another. These connection seams can often represent weakened areas of the implantable device, particularly when the bonds of these seams wear or break over time with repeated use or under stress. By manufacturing the disclosed implantable devices using additive manufacturing, connection seams are avoided entirely and therefore the problem is avoided.

In addition, by manufacturing these devices using an additive manufacturing process, all of the internal components of the device remain a complete construct during both the insertion process as well as the expansion process. That is, multiple components are provided together as a collective single unit so that the collective single unit is inserted into the patient, actuated to allow expansion, and then allowed to remain as a collective single unit in situ. In contrast to other cages requiring insertion of external screws or wedges for expansion, in the present embodiments the expansion and blocking components do not need to be inserted into the cage, nor removed from the cage, at any stage during the process. This is because these components are manufactured so as to be captured internally within the cages, and while freely movable within the cage, are already contained within the cage so that no additional insertion or removal is necessary.

In some embodiments, the cages can have an engineered cellular structure on a portion of, or over the entirety of, the cage. This cellular structure can include a network of pores, microstructures and nanostructures to facilitate osteosynthesis. For example, the engineered cellular structure can comprise an interconnected network of pores and other micro and nano sized structures that take on a mesh-like appearance. These engineered cellular structures can be provided by etching or blasting, to change the surface of the device on the nano level. One type of etching process may utilize, for example, HF acid treatment.

In addition, these cages can also include internal imaging markers that allow the user to properly align the cage and generally facilitate insertion through visualization during navigation. The imaging marker shows up as a solid body amongst the mesh under x-ray, fluoroscopy or CT scan, for example.

Another benefit provided by the implantable devices of the present disclosure is that they can be specifically customized to the patient's needs. Customization of the implantable devices is relevant to providing a preferred modulus matching between the implant device and the various qualities and types of bone being treated, such as for example, cortical versus cancellous, apophyseal versus central, and sclerotic versus osteopenic bone, each of which has its own different compression to structural failure data. Likewise, similar data can also be generated for various implant designs, such as for example, porous versus solid, trabecular versus non-trabecular, etc. Such data may be cadaveric, or computer finite element generated. Clinical correlation with, for example, DEXA data can also allow implantable devices to be designed specifically for use with sclerotic, normal, or osteopenic bone. Thus, the ability to provide customized implantable devices such as the ones provided herein allow the matching of the Elastic Modulus of Complex Structures (EMOCS), which enable implantable devices to be engineered to minimize mismatch, mitigate subsidence and optimize healing, thereby providing better clinical outcomes. It should be appreciated throughout the description below that the features, structures, and methods described with respect to one example of an intervertebral cage can be applied to all other examples of intervertebral cages unless indicated to the contrary.

Figure 1B:
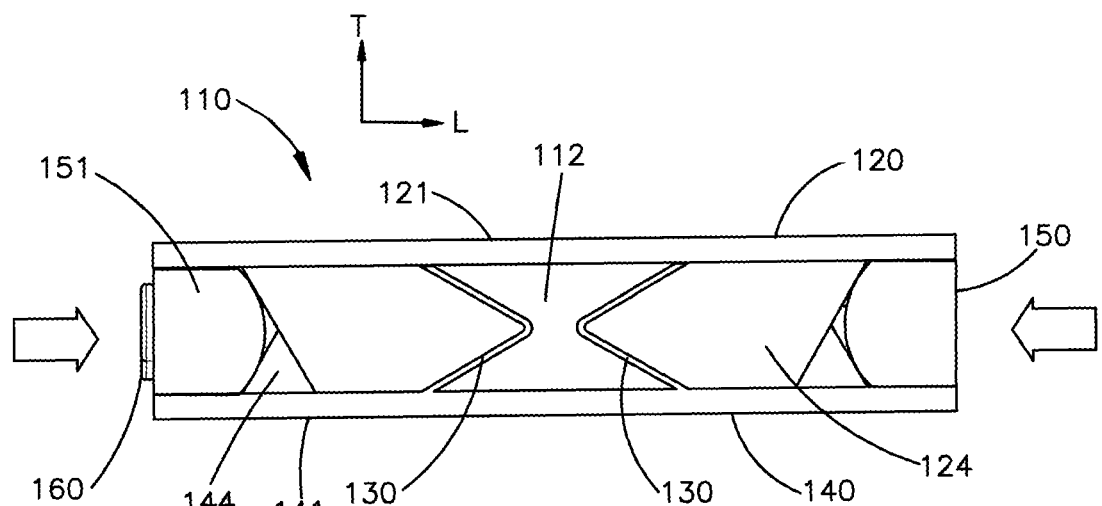
FIG. 1B is a side elevation view of the intervertebral cage illustrated in FIG. 1A.
Figure 1C:
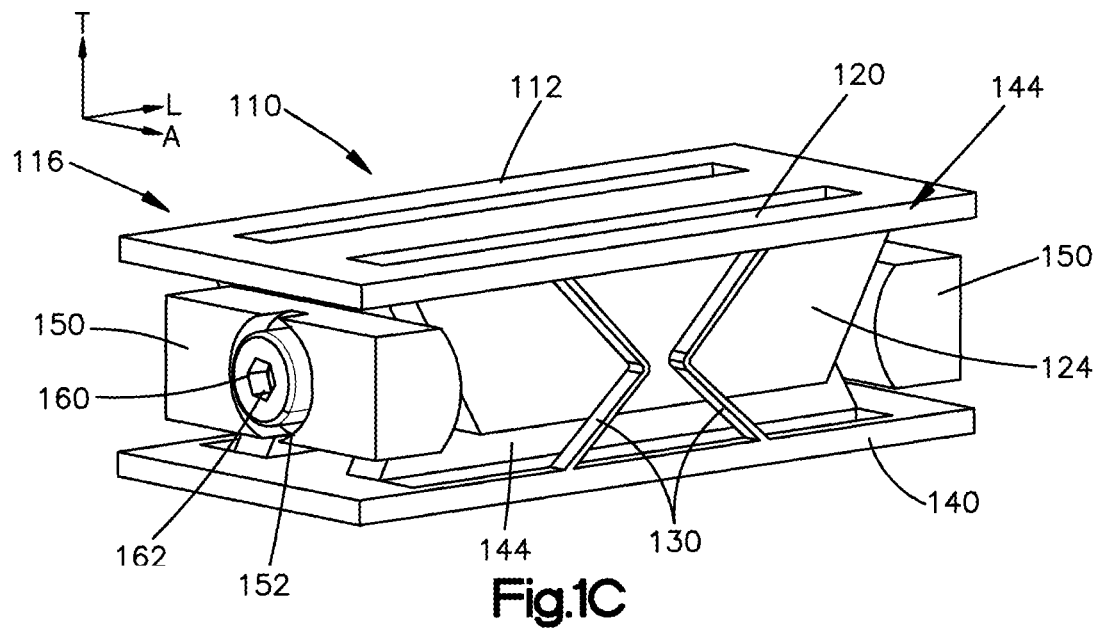
FIG. 1C is a perspective view of the intervertebral cage illustrated in FIG. 1A, shown in an expanded configuration.
Figure 1D:
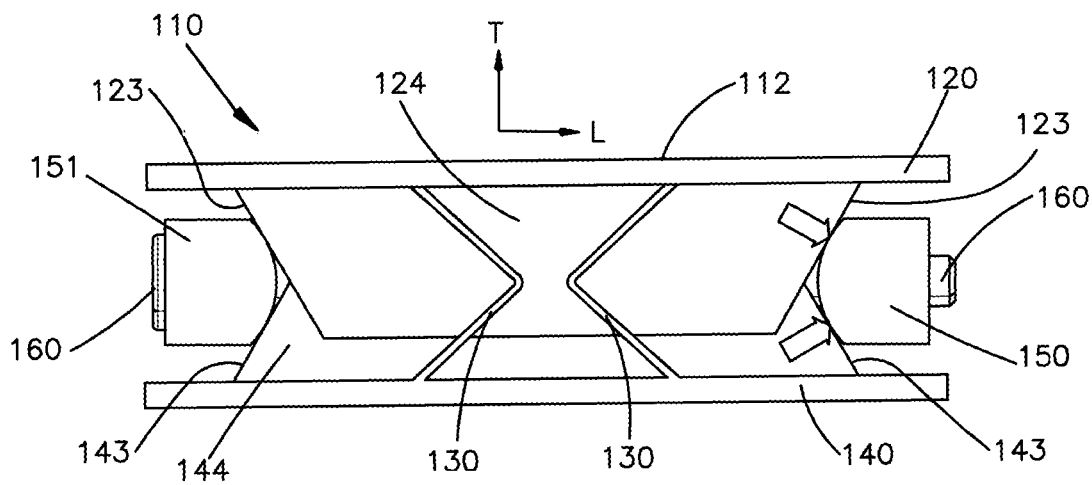
FIG. 1D is a side elevation view of the intervertebral cage illustrated in FIG. 1C.
Figure 1E:
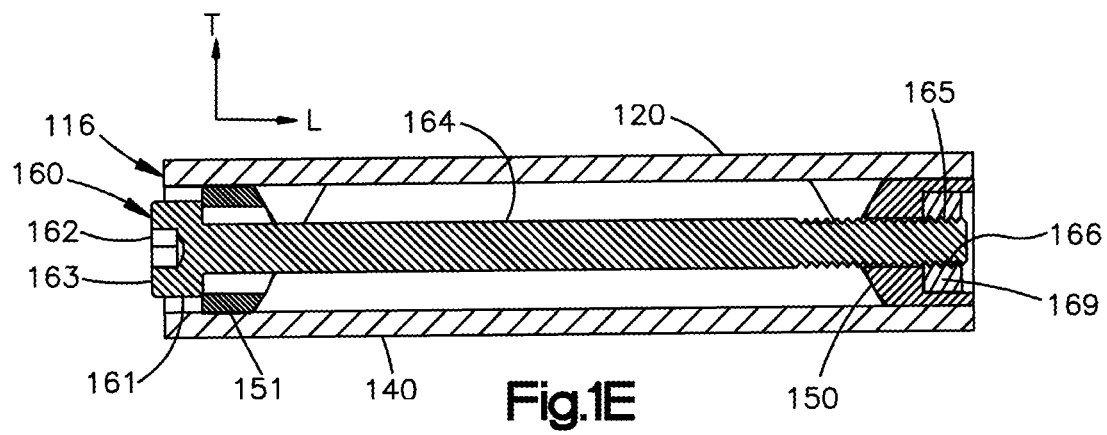
FIG. 1E is a sectional side elevation view of the intervertebral cage illustrated in FIG. 1C.
Figure 1F:
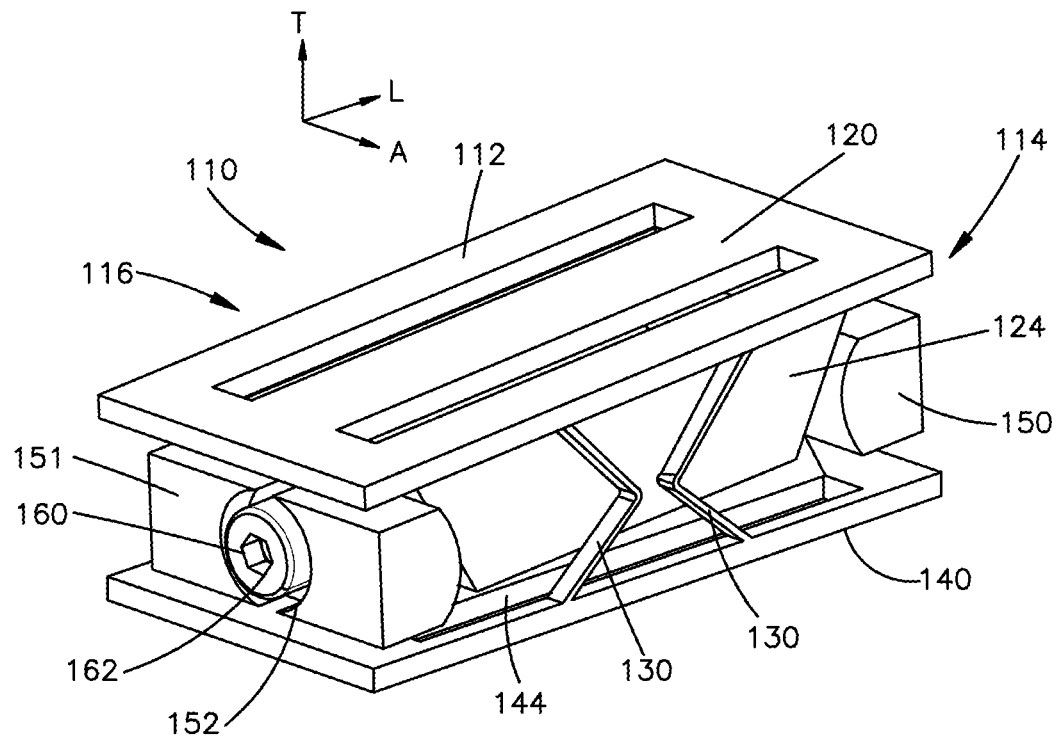
FIG. 1F is a perspective view of the intervertebral cage illustrated in FIG. 1A in an expanded and angularly adjusted configuration.
Figure 1G:
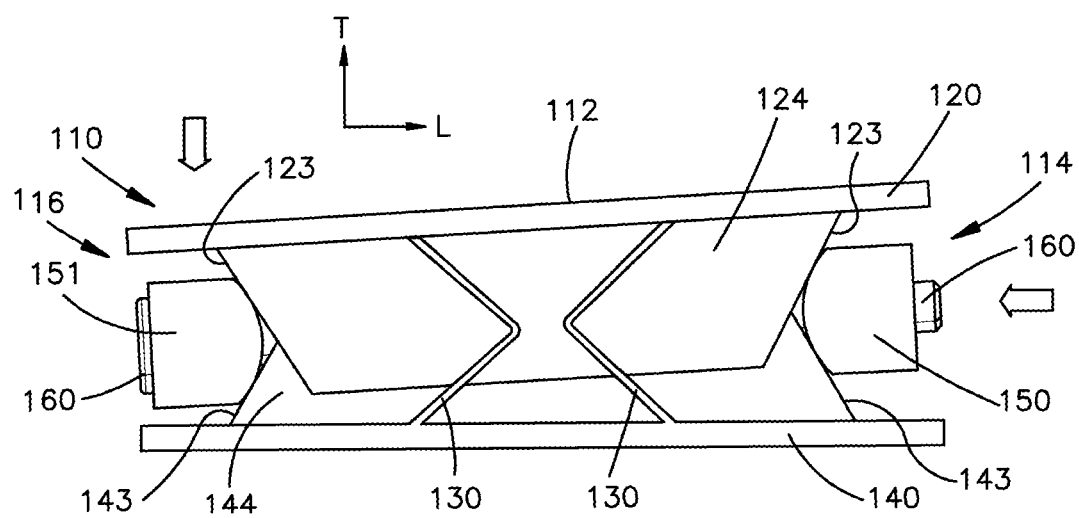
FIG. 1G is a side elevation view of the intervertebral cage illustrated in FIG. 1E.

Turning now to the drawings, FIGS. 1A to 1F illustrate one example of an expandable and angularly adjustable intervertebral cage 110 of the present disclosure. FIGS. 1A-1B show the intervertebral cage 100 in its first or insertion configuration. The insertion configuration can also be referred to as an unexpanded configuration. The intervertebral cage 110 includes a housing 112 that is defined by a superior or upper housing portion 119 and an inferior or lower housing portion 139. The upper housing portion 119 can include a superior or upper plate 120, and the lower housing portion 139 can include an inferior or lower plate 140. The upper and lower plates 120 and 140, respectively, are configured for placement against respective superior and inferior vertebral bodies. For instance, the upper plate 120 can define an outer or upper bearing surface 121 that is configured to abut an endplate of the superior vertebral body. Similarly, the lower plate 140 can define an outer or lower bearing surface 141 that is configured to abut an endplate of the inferior vertebral body. The upper and lower bearing surfaces 121 and 141 are spaced from each other along a transverse direction T. In one example, the bearing surfaces 121 and 141 can be flat for placement against the endplates. It is understood, of course, that the bearing surfaces 121 and 141 may also be sloped as desired. For instance, the bearing surfaces 121 and 141 can be convex and rounded if desired. Further, the upper and lower bearing surfaces 121 and 141 can be defined by flexible slats that are spaced from each other along the lateral direction A, and elongate along the longitudinal direction L.

The intervertebral cage 110 can define a first, leading end 114 with respect to insertion into an intervertebral disc space defined between the superior and inferior vertebrae. The intervertebral cage 110 can further define a second, trailing end 116 opposite the leading end 114 along a longitudinal direction L. The longitudinal direction L can be oriented perpendicular to the transverse direction T. Thus, the intervertebral cage 110 can define a leading direction that extends from the trailing end 116 toward the leading end 114. Thus, leading components of the intervertebral cage 110 can be spaced from trailing components of the intervertebral cage in the leading direction. The intervertebral cage 110 can similarly define a trailing direction that extends from the leading end 114 toward the trailing end 116.

The upper housing portion 119 can further include upper sidewalls 124 that extend from the upper plate 120. For instance, the upper sidewalls 124 can extend down from the upper plate 120 along the transverse direction T. The upper sidewalls 124 can be spaced from each other along a lateral direction A. The lateral direction A can be oriented perpendicular to each of the longitudinal direction L and the transverse direction T. In one example, the transverse direction T can define a vertical direction during use. The lateral and longitudinal directions A and L can define horizontal directions during use. The lower housing portion 139 can include lower sidewalls 144 that extend from the lower plate 140. For instance, the lower sidewalls 144 can extend up from the lower plate 140 along the transverse direction T. The lower sidewalls 144 can be spaced from each other along the lateral direction A. The upper and lower sidewalls 124 and 144 can be configured to slide along one another. Thus, the upper and lower plates 120 and 140 can be translatable and rotatable in relation to each other vertically.

The upper and lower housing portions 119 and 139 can be sloped. That is, the upper and lower housing portions 119 and 139 can define upper and lower sloped engagement surfaces 123 and 143, respectively (see FIG. 1D). For instance, one of the upper sloped engagement surfaces 123 can be a leading upper sloped engagement surface, and the other of the upper sloped engagement surface 123 can be a trailing upper sloped engagement surface. Similarly, one of the lower sloped engagement surfaces 143 can be a leading lower sloped engagement surface, and the other of the lower sloped engagement surface 143 can be a trailing lower sloped engagement surface. In one example, the upper and lower sloped engagement surfaces 123 and 143 can be defined by the upper and lower sidewalls 124 and 144, respectively. For instance, the upper and lower sloped engagement surfaces 123 and 143 can be defined by longitudinally outermost surfaces of the upper and lower sidewalls 124 and 144, respectively.

The engagement surfaces 123 and 143 can be angled, rounded, or otherwise angularly offset with respect to the transverse direction T as they extend in the longitudinal direction L. For instance, the leading engagement surfaces 123 and 143 can flare toward the trailing end as they extend away from the respective upper and lower plates 120 and 140. Similarly, the trailing engagement surfaces 123 and 143 can flare toward the leading end as they extend away from the respective upper and lower plates 120 and 140.

The intervertebral cage 110 can further include at least one elastically deformable strip 130 that is configured to control the movement of the upper and lower sidewalls 124 and 144, respectively, relative to one another. The elastically deformable strips 130 can be attached to each of the upper housing portion 119 and the lower housing portion 139. The elastically deformable strips 130 can have a spring constant that allows but resists movement of the upper and lower housing portions 119 and 139 relative to each other. In this regard, the elastically deformable strips 130 can be referred to as spring members that can be configured as strips or any suitable alternative configuration as desired. The elastically deformable strips 130 can be located outboard of the sidewalls 124 and 144 with respect to the lateral direction A, as shown in FIG. 1A.

The intervertebral cage 110 can further include an integrated expansion and angular adjustment mechanism that is fully integrated within the intervertebral cage 110. The angular adjustment mechanism can be disposed between the upper and lower plates 120 and 140, respectively. For instance, the angular adjustment mechanism can be disposed between the upper plate 120 and the lower plate 140 with respect to the transverse direction T. The angular adjustment mechanism can include a driver component 160 and at least one wedge 150. For instance, the angular adjustment mechanism can include first and second wedges 150 and 151, respectively. The first and second wedges 150 and 151 can be disposed opposite each other with respect to the longitudinal direction L. For instance, the first wedge 150 can be a leading wedge, and the second wedge 151 can be a trailing wedge. One or both of the wedges 150 and 151 can include an opening or bore 152 that receives the driver component 160. In one example, the bore 152 is a central bore.

The driver component 160 can extend along a central axis. The central axis can extend along the longitudinal direction L. In one example, as descried in more detail below, the driver component 160 is configured to be actuated or driven so as to draw or pull at least one or both of the wedges 150 and 151 toward the other of the wedges 150 and 151.

The wedges 150 and 151 can have outer engagement surfaces that can be angled, rounded, or otherwise angularly offset with respect to the transverse direction T as they extend in the longitudinal direction L. For instance, the engagement surfaces can be rounded convex surfaces. In one example, the leading wedge 150 can define upper and lower engagement surfaces flare toward the trailing wedge 151 as they extend away from the upper and lower plates 120 and 140, respectively. In one example, the upper and lower engagement surfaces of the leading wedge 150 can combine so as to define a constant and continuously rounded convex engagement surface. Similarly, the trailing wedge 151 can define upper and lower engagement surfaces flare toward the leading wedge 150 as they extend away from the upper and lower plates 120 and 140, respectively. In one example, the upper and lower engagement surfaces of the trailing wedge 151 can combine so as to define a constantly rounded convex engagement surface.

When the wedges 150 and 151 are drawn, pulled, or otherwise moved toward each other along the longitudinal direction L, the upper and lower engagement surfaces of the leading wedge 150 bear against the respective leading upper and lower sloped engagement surfaces 123 and 143, respectively. Similarly, the upper and lower engagement surfaces of the trailing wedge 151 bear against the respective trailing upper and lower sloped engagement surfaces 123 and 143, respectively. The result is that the housing 112 expands from the first or insertion configuration illustrated in FIGS. 1A-1B to the second or expanded configuration illustrated in FIGS. 1C-1D. In particular, the wedges 150 and 151 urge the upper and lower housing portions 119 and 139 to move away from each other along the transverse direction T. Accordingly, the upper and lower bearing surfaces 121 and 141 move away from each other along the transverse direction T. When the intervertebral cage 110 is in the first or initial configuration, the upper and lower bearing surfaces 121 and 141 are spaced apart from each other a first distance along the transverse direction T. when the intervertebral cage 110 is in the second or expanded configuration, the upper and lower bearing surfaces 121 and 141 are spaced apart from each other a second distance along the transverse direction T that is greater than the first distance. As the upper and lower bearing surfaces 121 and 141 move away from each other, the upper and lower sidewalls 124 and 144 slide along each other.

The upper and lower bearing surfaces 121 and 141 define a first relative angular orientation with respect to each other when the intervertebral cage 110 is in the first or initial configuration. The spring member 130 can bias the upper housing portion 119 toward the first relative angular orientation. In one example, the upper and lower bearing surfaces 121 and 141 can be oriented parallel to each other in the first relative angular orientation. The upper and lower bearing surfaces 121 and 141 define a second relative angular orientation with respect to each other when the intervertebral cage 110 is in the second or expanded configuration. In one example, the second relative angular orientation can be the same as the first relative angular orientation. Thus, the upper and lower bearing surfaces 121 and 141 can be oriented parallel to each other in the second relative angular orientation.

In some examples, the intervertebral cage 110 can allow for angular adjustment of the upper and lower plates 120 and 140 relative to one another against the force of the spring 130. A drive assembly, including the driver component 160 and wedges 150 and 151, can be configured to float at least partially or fully within a housing assembly. The housing assembly can include the housing 112, including the upper and lower plates 120 and 140, and the elastic member, such as the spring 130, connected between the upper and lower plates 120 and 140. The driver component 160 can include a drive end 163 that can be configured to engage an actuation tool that is configured to drive the driver component 160. For instance, the actuation tool can be configured to rotate the driver component 160. The drive end 163 can, for instance, define an opening 162 that is configured to receive the actuation tool. The driver component can further include a shaft 164 that supports the first and second wedges 150 and 150.

The shaft 164 can be a threaded shaft 164 that has threads 165 at its distal end opposite the drive end 163. Thus, the threads 165 can be disposed at the front end of the shaft 164. The first wedge 150 can be configured to threadedly engage the shaft 164. For instance, the first wedge can carry internal threads 166 that are configured to threadedly mate with the threads 165 of the shaft 164. In one example, the first wedge 150 can receive a nut 169 that is not rotatable within the first wedge 150. The nut 169 can define the internal threads 166. Alternatively, the first wedge 150 can define the internal threads 166. Thus, as the shaft 164, and thus the driver component 160, rotates in a first direction of rotation, the threaded engagement applies a force to the first wedge 150 toward the second wedge 151, which decreases the longitudinal distance between the first and second wedges 150 and 151. As the shaft 164, and thus the driver component 160, rotates in an opposite second direction of rotation, the threaded engagement applies a force to the first wedge 150 away from the second wedge 151, which increases the longitudinal distance between the first and second wedges 150 and 151.

The second wedge member 151 can be configured to translate freely along the shaft 164. In particular, the second wedge member 151 can translate along the shaft 164 toward and away from the first wedge member 150 without actuating the shaft 164. It is recognized, however, that a load applied to the plates 120 and 140 will cause the second ramp 151 to abut a stop member 167 of the driver component 160 that prevents the second wedge 151 from backing off of the shaft 164. Alternatively, the first wedge 150 can be freely slidable along the shaft 164. Thus, both of the wedges 150 and 151 can be freely slidable along the shaft 164. Alternatively, one of the wedges 150 and 151 can be freely slidable along the shaft 164, while the other of the wedges 150 and 151 can be threadedly engaged with the shaft 164. During operation, as the shaft 164 is rotated in the first direction of rotation, the first wedge 150 is threadedly drawn toward the second wedge 151. However, one or both of the first and second wedges 150 and 151 can move toward the other of the first and second wedges 150 and 151, depending on the load applied to the cage 110.

That is, the first wedge 150 can move toward the second wedge 151 along the longitudinal direction L while the second wedge 151 remains stationary with respect to movement along the longitudinal direction L. Alternatively, the second wedge 151 can move toward the first wedge 150 along the longitudinal direction L while the first wedge 150 remains stationary with respect to movement along the longitudinal direction L. Alternatively still, each of the first and second wedges 150 and 151 can move toward the other of the first and second wedges 150 and 151. In some examples, one of the first and second wedges 150 and 151 can move a greater distance than the other of the first and second wedges 150 and 151.

In particular, a compressive load applied to one end of the cage 110 will cause the plates 120 and 140 to apply a compressive force to the corresponding wedge. Thus, a compressive load applied to the leading end 114 of the cage 110 causes the leading ends of the plates 120 and 140 to apply a compressive load to the leading wedge 150. As a result, actuation of the driver component 160 in the first direction can cause the trailing wedge 151 to move toward the leading wedge 150, as the leading wedge 150 is maintained stationary due to frictional forces between the leading wedge 150 and the upper and lower plates 120 and 140 resulting from the compression of the plates 120 and 140 against the leading wedge. Accordingly, the cage 110 will angulate such that the trailing end 116 has a height greater than the leading end 114.

Conversely, a compressive load applied to the trailing end 116 of the cage 110 causes the trailing ends of the plates 120 and 140 to apply a compressive load to the trailing wedge 151. As a result, actuation of the driver component 160 in the first direction can cause the leading wedge 150 to move toward the trailing wedge 151, as the trailing wedge 151 is maintained stationary due to frictional forces between the trailing wedge 151 and the upper and lower plates 120 and 140 resulting from the compression of the plates 120 and 140 against the trailing wedge 151. Accordingly, the cage 110 will angulate such that the leading end 114 has a height greater than the trailing end 116 (see FIG. 1F).

Alternatively still, if the load applied to the cage 110 is uniform, the first and second wedges 150 and 151 can travel equal distances along the longitudinal direction L, and the relative orientation of the upper and lower plates 120 and 140 prior to expansion will equal the relative orientation of the upper and lower plates 120 and 140 after expansion.

Thus, it should be appreciated that the wedges 150 and 151 can adopt a relative position that is based on a load distribution on the plates 120 and 140. The load distribution can be applied by the anatomical load once the intervertebral cage 110 has been implanted in the intervertebral space. Depending on the orientation of the load, expansion of the cage 110 along the transverse direction T will stop on one side and can be continued on the other side as the cage 110 is expanded until the plates 120 and 140 are in complete contact with the respective vertebral endplates. Thus, the intervertebral cage 110 may be angularly adjustable and expandable with an integrated expansion and angular adjustment mechanism that is entirely contained within the housing 112. In this regard, the second relative angular orientation can be different than the first relative angular orientation. It is contemplated that normal anatomical loads will not cause the wedges 150 and 151 to move away from each other along the longitudinal direction L.

The driver component 160 may have a tool-engaging opening 162 to attach to a tool for actuation. The tool can be configured to drive the driver component 160 to draw the wedges 150 and 151 toward each other to expand the implant, and can further be configured to cause the wedges 150 and 151 to separate from each other. It is contemplated that any type of driving mechanism may be employed for the driver component 160. For example, one may be a threaded screw or bolt mechanism, while in another example the driving mechanism may be a push-pull mechanism. In another example, the driving mechanism may employ a pulley type mechanism, and in still another example, the driving mechanism may employ a tie wrap or elastically deformable capture mechanism.

FIGS. 2A to 2G illustrate another example of an expandable and angularly adjustable intervertebral cage 210 of the present disclosure. Like the intervertebral cage 110 described above with respect to FIGS. 1A-1F, this intervertebral cage 210 can include a housing 212 that, in turn, includes an upper housing portion 219 and a lower housing portion 239. The upper housing portion 219 includes an upper plate 220 that defines an upper bearing surface 221. The lower housing portion 239 includes a lower plate 240 that defines a lower bearing surface 241. The upper and lower plates 220 and 240, respectively, are configured for placement against endplates of a pair of adjacent vertebral bodies in an intervertebral space that is defined between the vertebral bodies. In one example, the bearing surfaces 221 and 241 can be flat for placement against the endplates. It is understood, of course, that the bearing surfaces 221 and 241 may also be sloped as desired. For instance, the bearing surfaces 221 and 241 can be convex and rounded if desired. Further, the upper and lower bearing surfaces 221 and 241 can be defined by flexible slats that are spaced from each other along the lateral direction A, and elongate along the longitudinal direction L.

The upper housing portion 219 can include upper sidewalls 224 that extend down from the upper plate 220, and the lower housing portion 239 can include lower sidewalls 244 that extend up from the lower plate 240. The sidewalls 224 and 244 are configured to slide along each other, and can allow the upper and lower housing portions 219 and 239, and thus the upper and lower plates 220 and 240, to translate and rotate in relation to each other vertically, as explained below. Further, as shown in FIG. 2B, the upper housing portion 219 can include a plurality of pairs of protrusions 228a-228c that extend out from the upper sidewalls 224 proximate to a lowermost end of the upper sidewalls 224. The protrusions 228a-228c can be configured as rounded knobs or protrusions, or any alternative geometry as desired. The first protrusions 228a can be positioned as first outer projections, the second protrusions 228b can be positioned as second outer projections, and the third protrusions 228c can be configured as middle outer projections that are disposed between the first and third outer projections along the longitudinal direction L.

One of the upper and lower housing portions 219 and 239 can include at least one seat 236, and the other of the upper and lower housing portions 219 and 239 can include a spring member 230 having a free end that bears against the seat. In one example, the lower housing portion 239 can include the spring member 230 that extends along one or both of the lower sidewalls 244. The upper plate 220 can include the at least one seat that extends out from the upper sidewall 224. The at least one seat can be in in the form of semi-circular or rounded pins 226, or any suitable alternative geometry, that extends out from the upper sidewalls proximate to an upper end of the upper sidewalls 224. The combination of the elastically deformable spring 230 and the pins 226 form an elastic interconnection between the upper and lower housing portions 219 and 239, and thus also between the upper and lower plates 220 and 240, as shown in FIG. 2A.

The intervertebral cage 210 can further include an integrated expansion and angular adjustment mechanism that is fully integrated within the intervertebral cage 210. The angular adjustment mechanism can be disposed between the upper and lower plates 220 and 240, respectively. For instance, the angular adjustment mechanism can be disposed between the upper plate 220 and the lower plate 240 with respect to the transverse direction T. The angular adjustment mechanism can include at least one wedge. For instance, the angular adjustment mechanism can include first and second wedges 250 and 251, respectively. The first and second wedges 250 and 251 can be disposed opposite each other with respect to the longitudinal direction L. It should thus be appreciated that the intervertebral cage 210 can consist of four (4) separate components that can be manufactured or SLM printed in one run. The four separate components can be defined by the upper hosing portion 219, the lower housing portion 239, the first wedge 250, and the second wedge 251.

The first wedge 250 can be aligned with a first portion of the upper plate 220 along the transverse direction T. Similarly, the second wedge 251 can be aligned with a second portion of the upper plate 220 along the transverse direction T. Because the wedges 250 and 251 are movable along the longitudinal direction L, the location of the first and second portions of the upper plate 220 can likewise vary as the wedges 250 and 251 move.

The wedges 250 and 251 can have engagement surfaces that can be angled, rounded, or otherwise angularly offset with respect to the transverse direction T as they extend in the longitudinal direction L. For instance, the engagement surfaces can be straight linear surfaces. In one example, each wedge 250 and 251 can include a pair of laterally opposed sloped slots 258 that define the engagement surfaces. The sloped slots 258 of the first wedge 250 can be sloped toward the second wedge 251 as they extend away from the upper plate 220 along the transverse direction T. Similarly, the sloped slots 258 of the second wedge 251 can be sloped toward the first wedge 250 as they extend away from the upper plate 220 along the transverse direction T. As will be appreciated from the description below, the sloped slots 258 of the first and second wedges 250 and 251 are configured to receive the protrusions 228a and 228b, respectively, so as to cause at least a portion of the first plate 220 to move away from the second plate 240 along the transverse direction T, thereby expanding and/or angulating the cage 210. The lower plate 240 can remain stationary during movement of the upper plate 220.

The lower plate 240 may include at its far longitudinal ends a pair of stop members 246 that can prevent the wedges 250 and 251 from backing out of the housing 212. The lower housing portion 239 can further include at least one guide rail 248 that is configured to be received by a corresponding channel 256 that extends through the wedges 250 and 251 along the longitudinal direction L. The at least one guide rail 248 can be oriented along the longitudinal direction L. Further, the at least one guide rail 248 can extend along a transverse inner surface of the lower plate 240. In one example, the lower housing portion 239 can include first and second guide rails 248 that are spaced from each other along the lateral direction A and are received in respective channels 256 of the wedges 250 and 251. The guide rails 248 can have outwardly projecting teeth 272 (see FIG. 2F). Similarly, the wedges 250 can include at least one complementary finger 274 in the channels 256 that is configured to engage and interlock with the teeth 272 of the guide rails 248 (see FIG. 2F).

During operation, the wedges 250 can be deployed individually and are configured to slide individually along the guide rails 248 along the longitudinal direction L. The sloped slots 258 of the first wedge member 250 receive the first protrusions 228a, and the sloped slots 258 of the second wedge member 251 receive the third protrusions 228b. Thus, as shown in FIG. 2C, as each of the members 250 and 251 translates longitudinally toward the other wedge member 250 and 251, the engagement surfaces of the wedge members 250 and 251 defined by the sloped slots 258 bear against the first and second protrusions 228a and 228b, respectively, which urges the upper housing portion 219, and thus the upper plate 220, to move away from the lower housing portion 239, and thus the lower plate 240, along the transverse direction T.

Figure 2C:
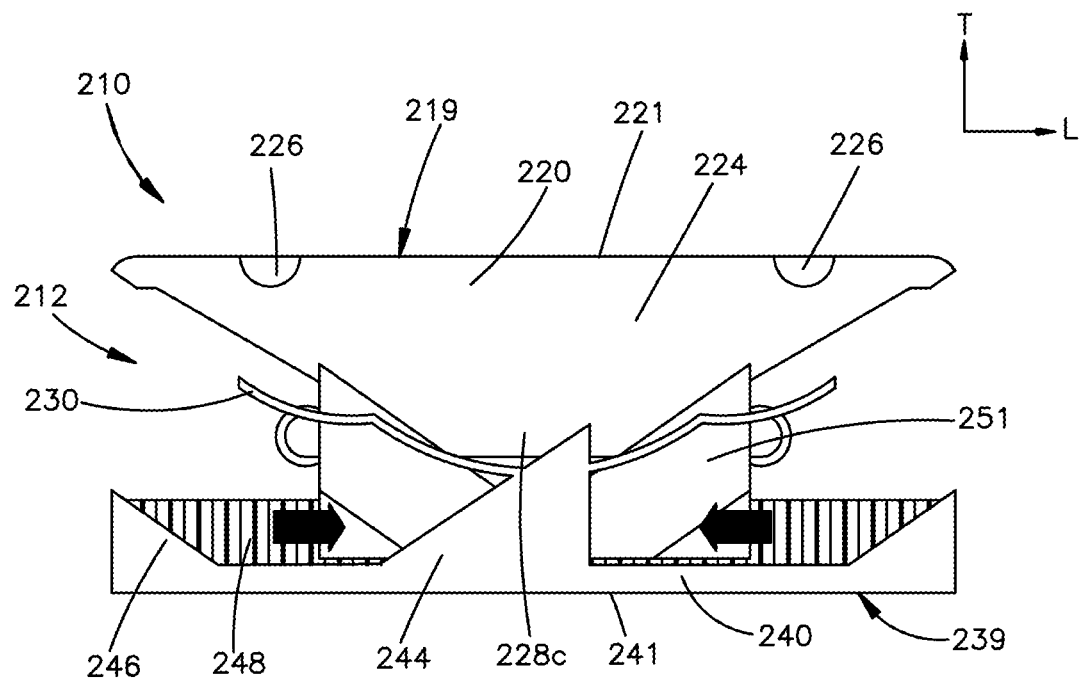
FIG. 2C is a side elevation view of the intervertebral cage illustrated in FIG. 2A shown in an expanded configuration.

The lower housing portion 239 can define a transverse slot 253 that extends into each of the lower sidewalls 244 (see FIG. 2B). The transverse slots 253 are configured to receive the third protrusion 228c. Alternatively, the upper housing portion 219 can define the transverse slot 253 that extends into each of the upper sidewalls, and the third protrusion 228c can be carried by the lower housing portion 239. The third protrusions 228c can ride along the transverse slots 253 as the upper housing portion 219 moves relative to the lower housing portion 239 along the transverse direction. It should be appreciated that the middle protrusion 228c travels along the vertical or transverse direction T in the transverse slot 25, while the first and second protrusions 228a and 228b ride in the sloped slots 258 that are angled with respect to the transverse direction T. As illustrated in FIGS. 2A and 2C, the first relative angular orientation of the plates 220 and 240 prior to expansion can equal the second relative angular orientation of the plates 220 and 240 after expansion.

Figure 2D:
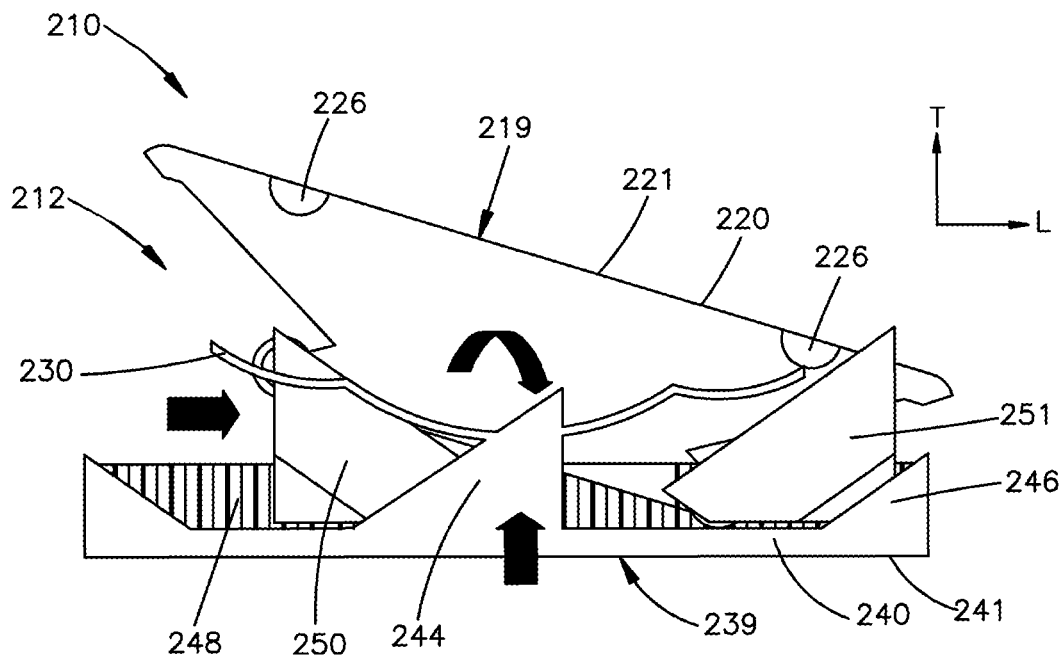
FIG. 2D is a lateral view of the intervertebral cage illustrated in FIG. 2A shown in an expanded and angularly adjusted configuration.
Figure 2E:
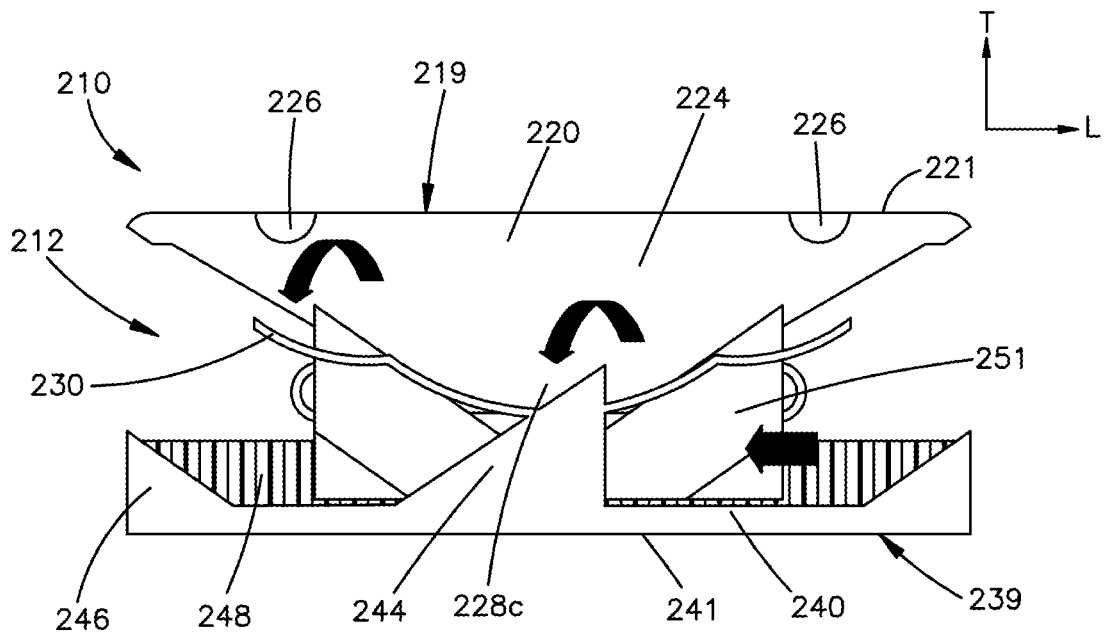
FIG. 2E is a lateral view of the intervertebral cage illustrated in FIG. 2A shown having moved from the expanded and angularly adjusted configuration illustrated in FIG. 2D to the expanded configuration.

Referring now to FIG. 2D, the wedges 250 and 251 can be separately deployable and independently movable. Independently moving one of the wedges 250 and 251 can cause angular adjustment of the intervertebral cage 210. In particular, independently moving the wedges 250 and 251 can cause angular adjustment of the upper plate 220 with respect to the lower plate 240. For instance, by moving the first wedge 250 toward the second wedge 251 while maintaining the second wedge 251 stationary, the upper plate 220 may be angularly adjusted. In particular, the first portion of the upper plate 220 can move away from the lower plate 240 along the transvers direction T relative to the second portion of the upper plate 220. It should be appreciated that the upper plate 220 can angulate both when the second wedge 251 remains stationary, or when the first wedge 250 translates along the longitudinal direction at a disproportionate amount with respect to the translation of the second wedge 251 (both referred to as movement of the first wedge relative to the second wedge along the longitudinal direction L). Translation of both wedges 250 and 251 a disproportionate amount can cause the cage 210 to both expand along the transverse direction T and angulate. It should be further appreciated that the upper plate 220 can angularly adjust about the middle protrusion 228c as it is disposed in the transverse slot 253. Thus, the middle protrusion 228c can define a fulcrum for angular movement of the upper plate 220. Accordingly, the second relative angular orientation of the first and second plates 220 can be different than the second relative angular orientation of the first and second plates 220. It should be appreciated that an opposite angular adjustment can also be achieved by moving the second wedge 250 relative to the first wedge along the longitudinal direction L.

If it is desired to achieve the second relative angular orientation equal to the first relative angular orientation, the second wedge 251 can be moved longitudinally toward the first wedge 250, which urges the second location of the upper plate 220 to move relative to the first location of the upper plate 220 away from the lower plate 240 along the transverse direction. This causes the upper plate 220 to angulate about the middle protrusion 228c until the first and second portions of the upper plate 220 are equally spaced from the lower plate 240 along the transverse direction T. The resultant intervertebral cage 210 can have parallel upper and lower plates 220 and 240 in its second or expanded configuration. The first and second wedges 250 and 251 can be moved away from each other so as to urge the upper plate 220 to move toward the lower plate 240 along the transverse direction T, if it is desired to collapse the intervertebral cage 210. The sidewalls 224 and 244 can slide along each other as the cage 210 expands and angulates.

Figure 2F:
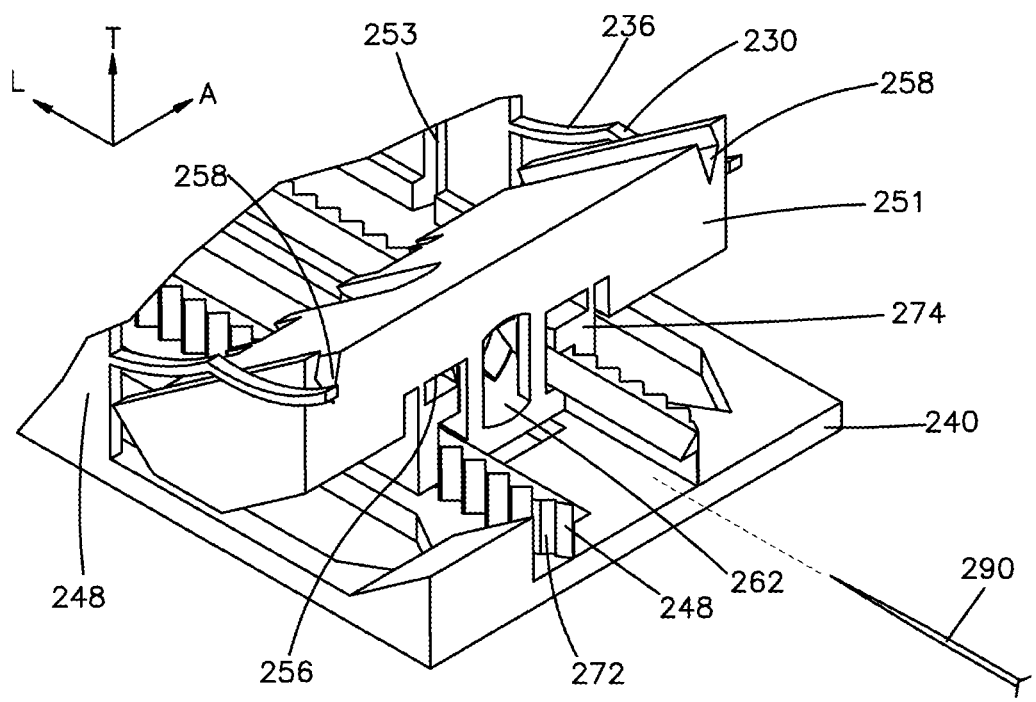
FIG. 2F is an enlarged view of a guide rail and wedge of the intervertebral cage illustrated in FIG. 2A.

Referring now to FIGS. 2F and 2G, and as described above, the housing 212 can define the guide rails 248, and the first and second wedges 250 and 251 can define the channels 256 that receive and ride along the guide rails 248 as the first and second wedges 250 and 251 translate longitudinally. The finger 274 can be a click finger 274 that is configured to ride along the teeth 272 as the wedges 250 and 251 move toward one another along the longitudinal direction L. However, the finger 274 can interlock with the teeth 272 so as to prevent movement of the first and second wedge members 250 and 251 away from each other in response to anatomical loading. Alternatively, the finger 274 can interlock with the teeth 272 so as to prevent movement of the first and second wedge members 250 and 251 both toward and away from each other. An implant assembly can include a bayonet type actuation instrument 290 that is insertable be inserted into a tool-engaging opening 262 of either wedge 250. The instrument 290 can be configured to urge the fingers 274 away from the teeth 272, thereby disengaging the fingers 274 from the teeth 272. Thus, engagement between the fingers 274 and the teeth 272 no longer prevents relative movement of the wedges 250 and 251 away from each other and, in some examples, toward each other. In one example, turning a bayonet-shaped end of the tool (for instance 90 degrees) can cause the fingers 274 to be urged away from the teeth 272, thereby unlocking the wedge 250 from the teeth 274. Releasing the instrument 290 can cause the fingers 274 to again engage the teeth 272, thereby locking the wedge 250 in place relative to the rails 248.

It is appreciated that the spring member 230 can provide a pre-tension that connect the upper housing portion 219 and the lower housing portion 239 together. The spring member 230 can be shaped to allow both vertical and angular movement of the type described above against the pre-tensioned spring force. The spring members 230 can be designed to only allow the movements described above.

FIGS. 3A to 3F illustrate yet another example of an expandable and angularly adjustable intervertebral cage 310 of the present disclosure. The intervertebral cage 310 can include an outer housing 312 and upper and lower housing portions 319 and 339 that are movable within the outer housing 312. The outer housing 312 can have an open top and bottom to accommodate movement of the upper and lower housing portions 319 and 339. The upper housing portion 319 can include an upper plate 320 and upper sidewalls 324 that extend down from the upper plate 320 along the transverse direction T. The lower housing portion 339 can include a lower plate 340 and lower sidewalls 344 that extend up from lower plate 340 along the transverse direction T. The upper and lower plates 320 and 340, respectively, can be configured to be placed against endplates of a pair of adjacent vertebral bodies. The upper plate 320 can define an upper bearing surface configured to abut a vertebral endplate of a superior vertebral body, and the lower plate 340 can define a lower bearing surface configured to abut a vertebral endplate of an inferior vertebral body. In one example, the bearing surfaces can be substantially flat. It is understood, of course, that the bearing surfaces can be shaped surfaces, such as convex, and rounded, if desired.

Figure 3A:
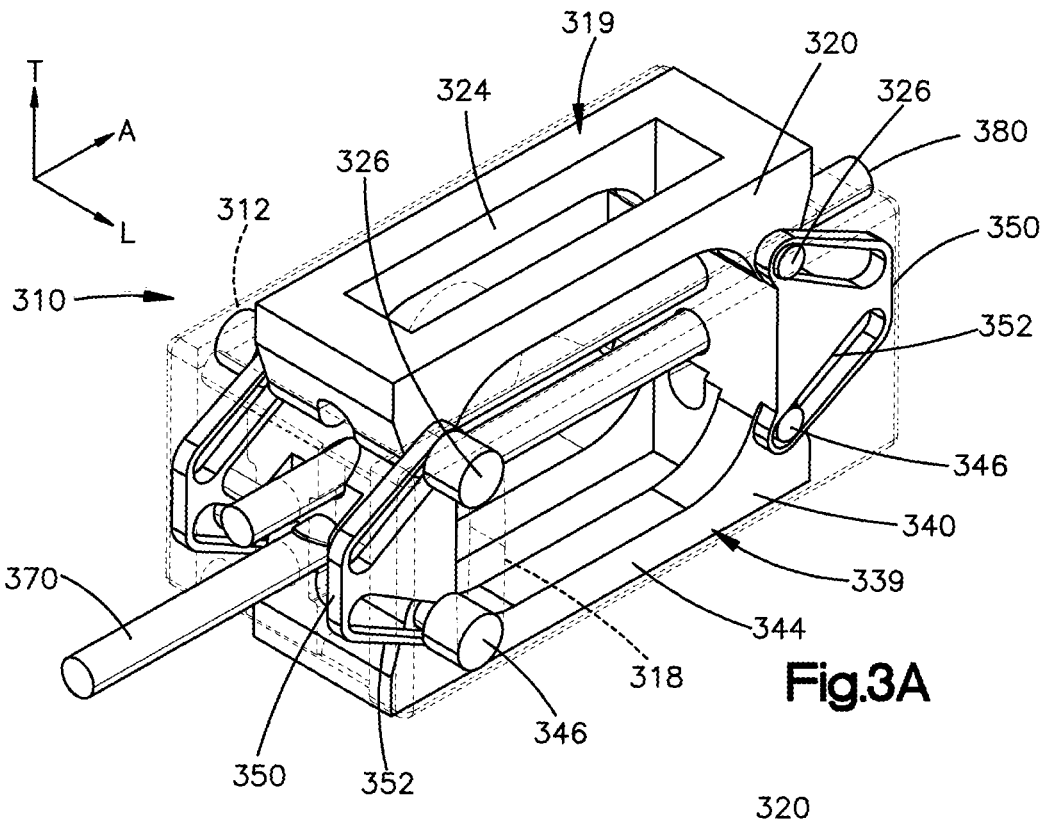
FIG. 3A is a partial cutaway view of an intervertebral cage constructed in accordance with another example, shown in an expanded configuration.
Figure 3B:
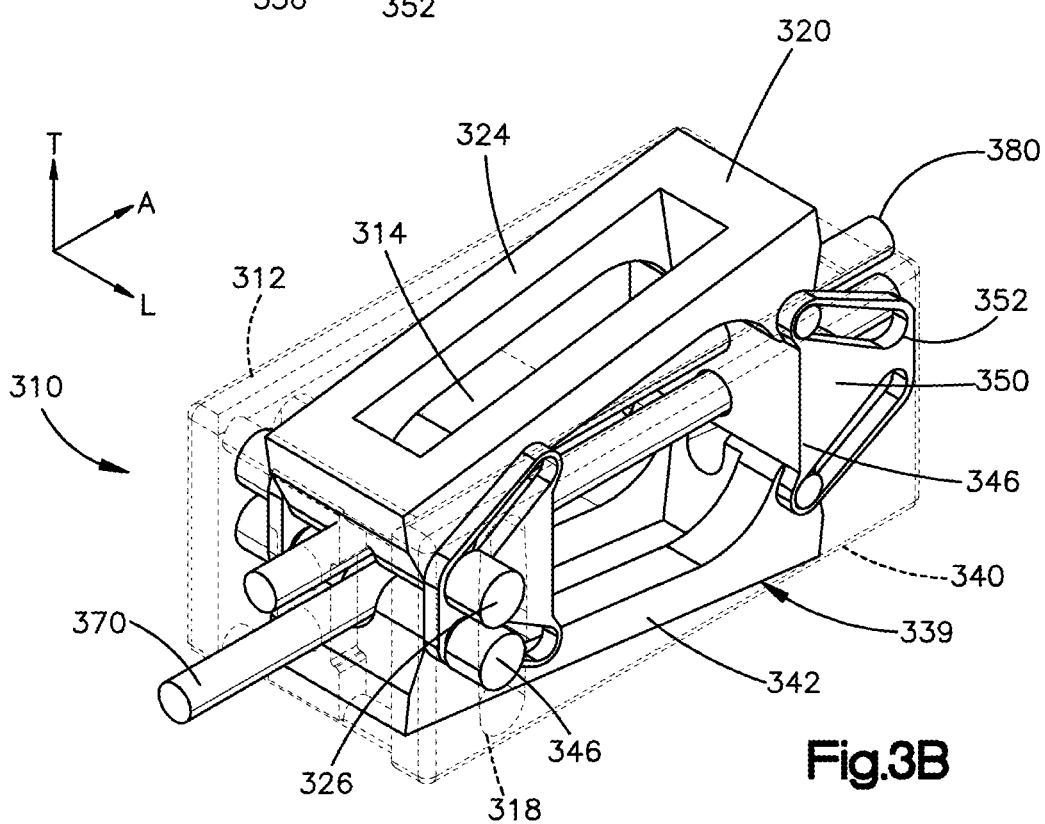
FIG. 3B is a partial cutaway view of the intervertebral cage illustrated in FIG. 3A in an angularly adjusted configuration.
Figure 3C:
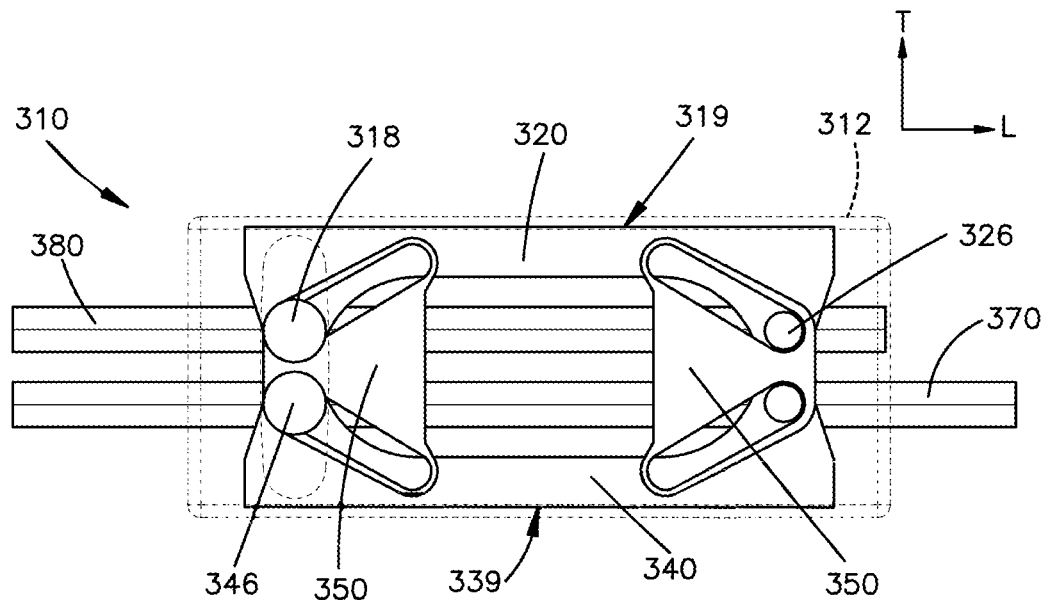
FIG. 3C is a sectional side elevation view of the intervertebral cage illustrated in FIG. 3A, shown in an initial or insertion configuration.

FIG. 3A shows the intervertebral cage 310 in an expanded configuration whereby a distance between the upper and lower plates 320 and 340 has increased along the transverse direction T. FIG. 3B shows the same intervertebral cage 310 in an expanded, and angularly adjusted, configuration, whereby a relative angular orientation between the upper and lower plates 320 and 340 have been changed.

With reference to FIGS. 3A-3B, the intervertebral cage 310 further includes an expansion and angular adjustment mechanism disposed between the upper and lower plates 320 and 340 with respect to the transverse direction T. The expansion and angular adjustment mechanism can include first and second brackets 350 and 351 that are disposed in the outer housing 312. The first and second brackets 350 and 351 can be configured as brackets in one example. The first bracket 350 can be aligned with both a first portion of the upper plate 320 and a first portion of the lower plate 340 along the transverse direction T. Similarly, the second bracket 351 can be aligned with a second portion of the upper plate 320 and a second portion of the lower plate 340 along the transverse direction T. Because the brackets 350 and 351 are movable along the longitudinal direction L as described below, the location of the first and second portions of the upper and lower plates 320 and 340 can likewise vary as the brackets 350 and 351 move.

Each of the first and second brackets 350 and 351 can have engagement surfaces that can be angled, rounded, or otherwise angularly offset with respect to the transverse direction T as they extend in the longitudinal direction L. For instance, the engagement surfaces can be straight linear surfaces. In one example, each bracket 350 and 351 can include a pair of laterally opposed sloped upper slots 352 and laterally opposed lower slots 353 that define the engagement surfaces. The upper sloped slots 352 of the first bracket 350 can be sloped away from the second bracket 351 as it extends away from the upper plate 320 along the transverse direction T. The upper sloped slots 352 of the second bracket 351 can be sloped away from the first bracket 350 as it extends away from the upper plate 220 along the transverse direction T. The lower sloped slots 353 of the first bracket 350 can be sloped away from the second bracket 351 as it extends away from the lower plate 340 along the transverse direction T. The lower sloped slots 353 of the second bracket 351 can be sloped away from the first bracket 350 as it extends away from the lower plate 340 along the transverse direction T. As will now be described, the sloped slots 258 and 259 are configured to receive projections of the upper and lower plate members 319 and 339 that urge the upper and lower plates 320 and 340 to move relative to each other along the transverse direction T, thereby expanding and/or angulating the cage 310.

In particular, the upper plate portion 319 can include first and second pairs of upper protrusions 326. The upper protrusions 326 can extend out from the upper sidewalls 324. Each of the pairs can be spaced from each other along the longitudinal direction L. Further, the upper protrusions 326 of each pair can be opposite each other along the lateral direction A. The upper protrusions 326 can be configured as knobs in one example. The protrusions 326 are sized to be received in the upper sloped slots 352, and freely slidable in the upper sloped slots 352. The first pair of upper protrusions 326 are configured to ride in the upper slots of the first bracket 350. The second pair of upper protrusions 326 are configured to ride in the upper slots of the second bracket 351.

Similarly, the lower plate portion 339 can include first and second pairs of lower protrusions 346. The lower protrusions 346 can extend out from the lower sidewalls 344. Each of the pairs can be spaced from each other along the longitudinal direction L. Further, the lower protrusions 346 of each pair can be opposite each other along the lateral direction A. The lower protrusions 346 can be configured as knobs in one example. The lower protrusions 346 are sized to be received in the lower sloped slots 353, and freely slidable in the lower sloped slots 353. For instance, the first pair of lower protrusions 346 are configured to be received in the lower sloped slots 353 of the first bracket 350. The second pair of lower protrusions 346 are configured to be received in the lower sloped slots 353 of the second bracket 351. Thus, the upper and lower protrusions 326 and 346 can define engagement surfaces that ride along respective engagement surfaces in the upper and lower slots 352 and 353 so as to cause the upper and lower housing portions 319 and 339 to move relative to each other along the transverse direction T.

The outer housing 312 can define a pair of transverse side channels 318 that are aligned in the lateral direction A with one of the protrusions 326 and 346 that extend through one of the brackets 350 and 351, illustrated as the first bracket 350. Thus, the upper and lower protrusions 326 and 346 that extend though the respective upper and lower slots 352 and 353 of the first bracket 350 can further extend into the channels 318. Because the side channels 318 are elongate along the transverse direction T, the engagement of the side channels 318 with the respective protrusions 326 and 346 prevents or limits longitudinal movement of the upper and lower plates 320 and 340. In one example, the outer housing 312 does not define any side channels 318 that receive the protrusions of the second bracket 351.

The intervertebral cage 310, and in particular the expansion and angular adjustment mechanism, can include a first actuation rod 370 that is translatably fixed to the first bracket 350 and longitudinally translatable with respect to the second bracket 351, and a second actuation rod 380 that is translatably fixed to the second bracket 351 and longitudinally translatable with respect to the first bracket 350. The first and second rods 370 and 380 can extend gripping ends that extend longitudinally out from the outer housing 312. Thus, the first bracket 350 moves longitudinally with the first actuation rod 370. Similarly, the second bracket 351 moves longitudinally with the second actuation rod 380. In one example, the first and second actuation rods 370 and 380 can be configured as pull rods that are configured to be pulled longitudinally to effect sliding longitudinal movement of the brackets 350 and 351.

As described above, first ones of the upper and lower protrusions 326 and 346 of the upper housing member 319 and lower housing member 339 are slidable in the upper and lower sloped slots 352 and 353, respectively, of the first bracket 350. This causes the distance between the first portions of the first and second plates 320 and 340 to change along the transverse direction. For instance, as the first bracket 350 is moved away from the second bracket 351, the first protrusions 326 and 346 push against the upper and lower housing portions 319 and 339. Thus, the distance between the first portions of the first and second plates 320 and 340 increases along the transverse direction T. As the first bracket 350 is moved toward the second bracket 351, the distance between the first portions of the first and second plates 320 and 340 decreases along the transverse direction T.

Similarly, second ones of upper and lower protrusions 326 and 346 of the upper housing member 319 and lower housing member 339 are slidable in the upper and lower sloped slots 352 and 353, respectively, of the second bracket 351. This causes the distance between the second portions of the first and second plates 320 and 340 to change along the transverse direction T. For instance, as the second bracket 351 is moved away from the first bracket 350, the second protrusions 326 and 346 push against the upper and lower housing portions 319 and 339. Thus, the distance between the second portions of the first and second plates 320 and 340 increases along the transverse direction T. As the second bracket 350 is moved toward the first bracket 350, the distance between the second portions of the first and second plates 320 and 340 decreases along the transverse direction T.

The first and second actuation rods 370 and 380 are configured to move longitudinally relative to the outer housing 312. Longitudinal movement of the rods 370 and 380 causes the respective brackets 350 and 351 affixed to the rod to be likewise moved longitudinally. In each of the brackets 350 are upper and lower angled slots 352 and 353, as described above. The slots 352 and 353 are integrated above and below each other, and angled in opposite directions. The slots 352 and 353 of the first bracket 350 are mirrored and can be deployed independently of the slots 352 and 353 of the second wedge member 351, and vice versa. The mechanism within the outer housing 312 enables the upper and lower plates 320, 340 to slide vertically at the hinge or pivot joints defined by the knobs 326, 346 within the angled slots 352. Further, the first protrusions 326 and 346 can slide within the transverse side channel 318 of the outer housing 312, while the second protrusions 326 and 346 can slide only within the respective slots of the second bracket 351.

Figure 3D:
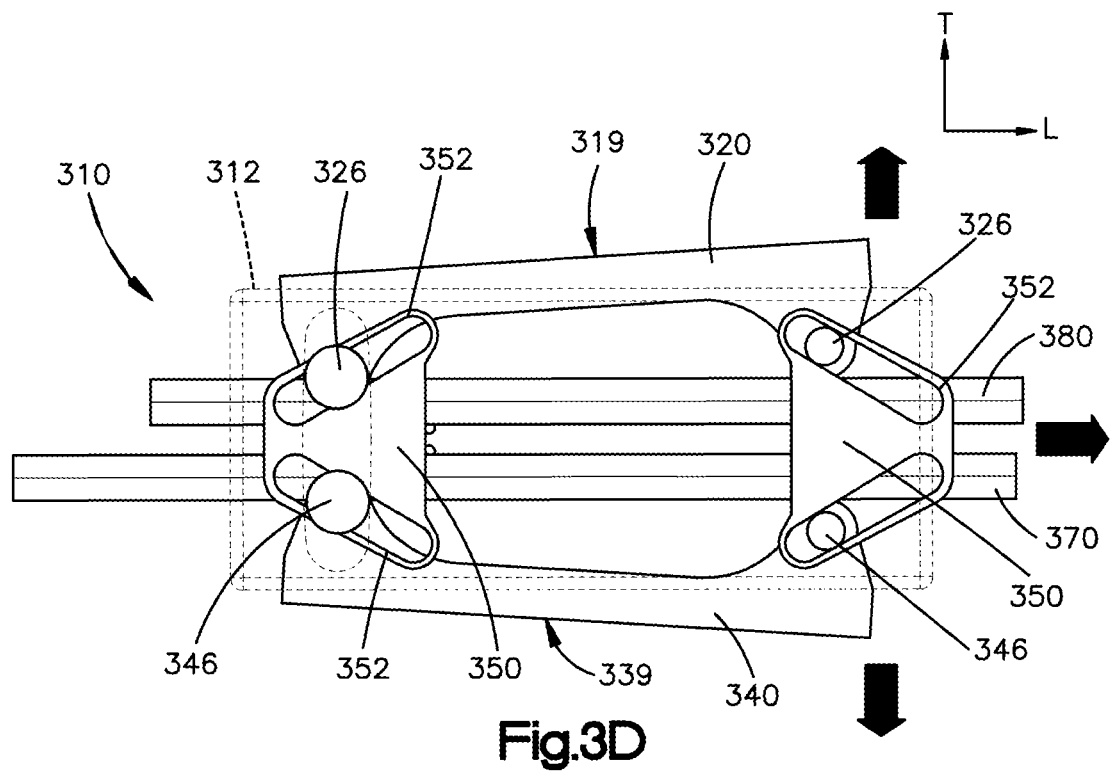
FIG. 3D is a sectional side elevation view of the intervertebral cage illustrated in FIG. 3C, shown during actuation from the insertion configuration to an angularly adjusted configuration.
Figure 3E:
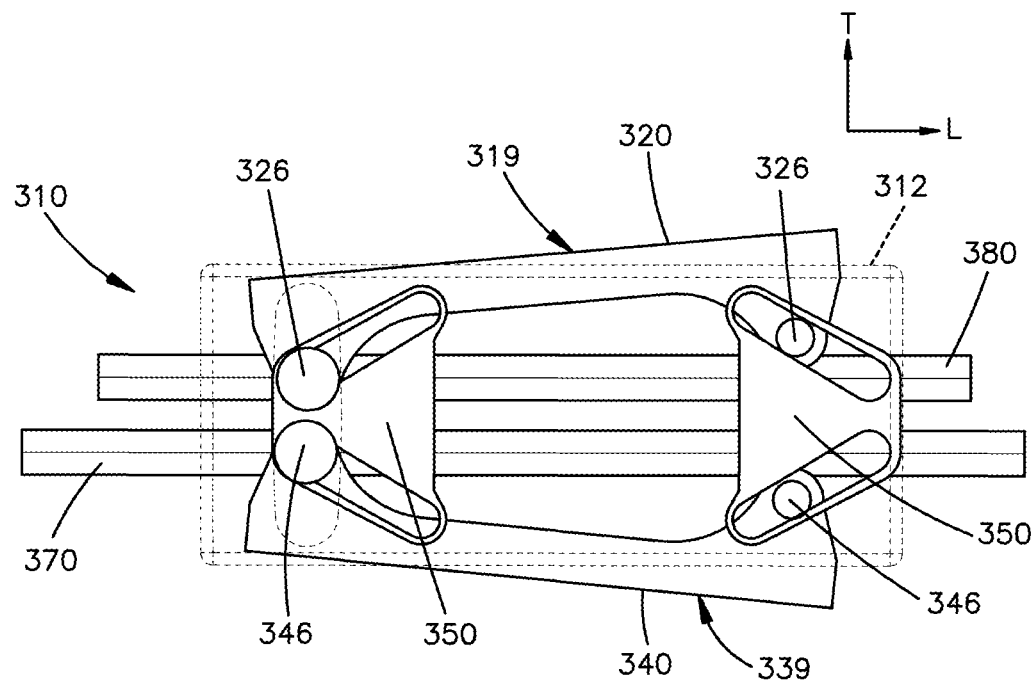
FIG. 3E is a sectional side elevation view of the intervertebral cage illustrated in FIG. 3D, but shown in a fully angularly adjusted configuration.

A method of actuating the intervertebral cage 310 will now be described with reference to FIGS. 3C-3F. In a starting position illustrated in FIG. 3C, with the intervertebral cage 310 in its first or insertion configuration, the upper and lower projections 326 and 346 are in the transverse innermost position of the respective slots 352 and 353, respectively. Further, the first projections 326 and 346 are in their respective transverse innermost positions in the side channels 318. Referring to FIG. 3D, when the second rod 380 is actuated to move the second bracket 351 longitudinally away from the first bracket 350, the second upper and lower protrusions 326 and 346 are forced upward and downward, respectively, by the angled slots 352 and 353 of the second bracket 351. Thus, the second portions of the upper and lower plates 320 and 340 are moved away from each other along the transverse direction T. The first portions of the upper and lower plates 320 and 340 can remain stationary with respect to relative movement along the transverse direction T, thereby effecting expansion and angular adjustment of the intervertebral cage 310 as shown in FIG. 3E. In particular, respective angular orientations of the upper and lower plates 320 and 340 can change with respect to the outer housing 312. Thus, it will be further appreciated that the second relative angular orientation of the cage 310 can be different than the first angular orientation of the cage 310.

Figure 3F:
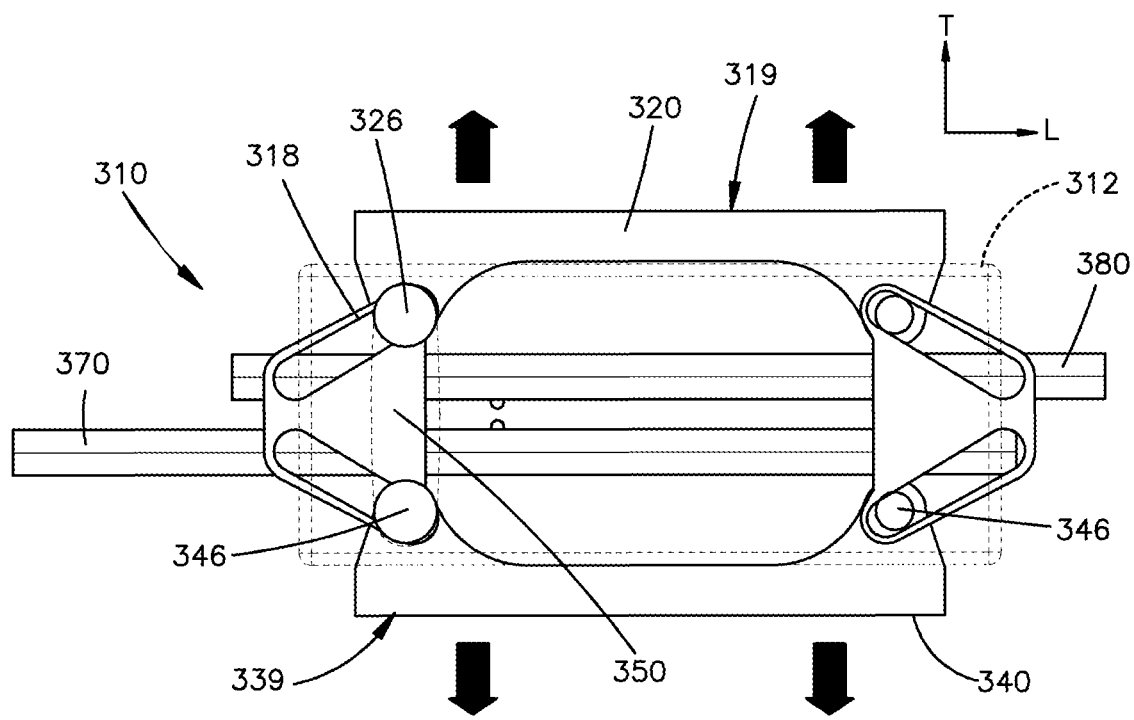
FIG. 3F is a sectional side elevation view of the intervertebral cage illustrated in FIG. 3E, but shown in the expanded configuration.

Referring now to FIG. 3F, when the first rod 370 is actuated to move the first bracket 350 longitudinally away from the second bracket 351, the first upper and lower protrusions 326 and 346 are forced upward and downward, respectively, by the angled slots 352 and 353 of the first bracket 350. Thus, the first portions of the upper and lower plates 320 and 340 are moved away from each other along the transverse direction T. The second portions of the upper and lower plates 320 and 340 can remain stationary with respect to relative movement along the transverse direction T. The first portions of the upper and lower plates 320 and 340 can expand vertically to a position whereby that the first and second plates 320 and 340 are in the same relative angular orientation as before expansion. Thus, the first relative angular orientation can be equal to the second relative angular orientation. Alternatively, the first portions of the upper and lower plates 320 and 340 can expand vertically to a position whereby that the first and second plates 320 and 340 are in a different relative angular orientation as before expansion.

Movement of the rods 370 and 380 can be restricted by the outer housing 312 to movement along the longitudinal direction L. Because the engagement between the first upper and lower protrusions 326 and 346 in the vertical channel 318, the upper and lower housing portions 319 and 339 are prevented from moving longitudinally. Further, the first upper protrusion 326 can define a fulcrum about which the second portion of the upper plate 320 can angulate when the second bracket 351 is moved away from the first bracket 350.

Figure 4A:
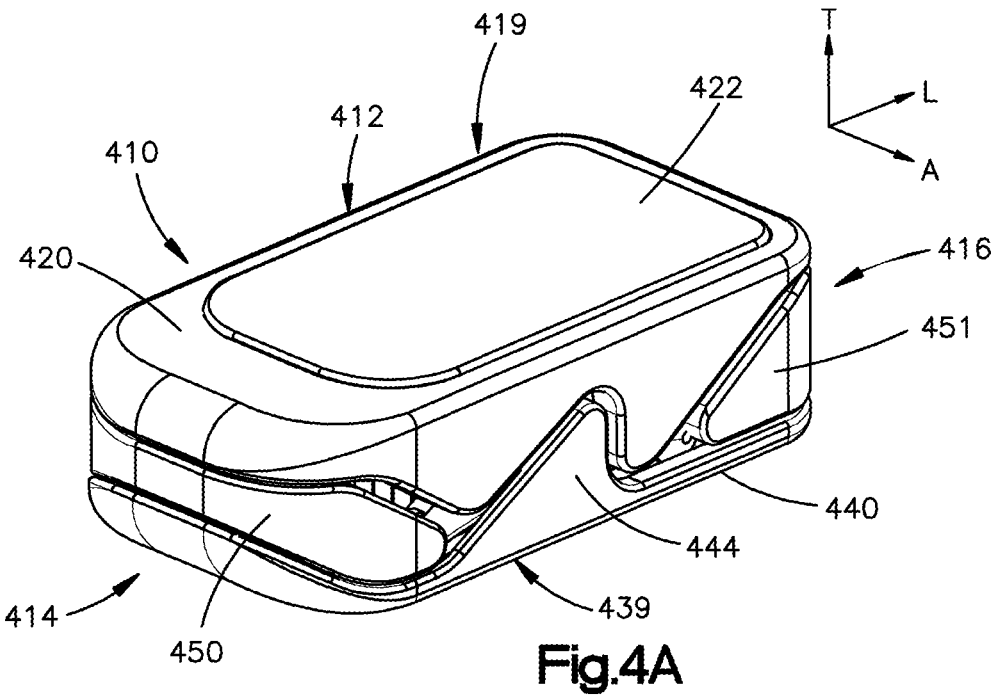
FIG. 4A is a perspective view of an intervertebral cage constructed in accordance with another example, configured for anterior lumbar interbody fusion (ALIF)
Figure 4B:
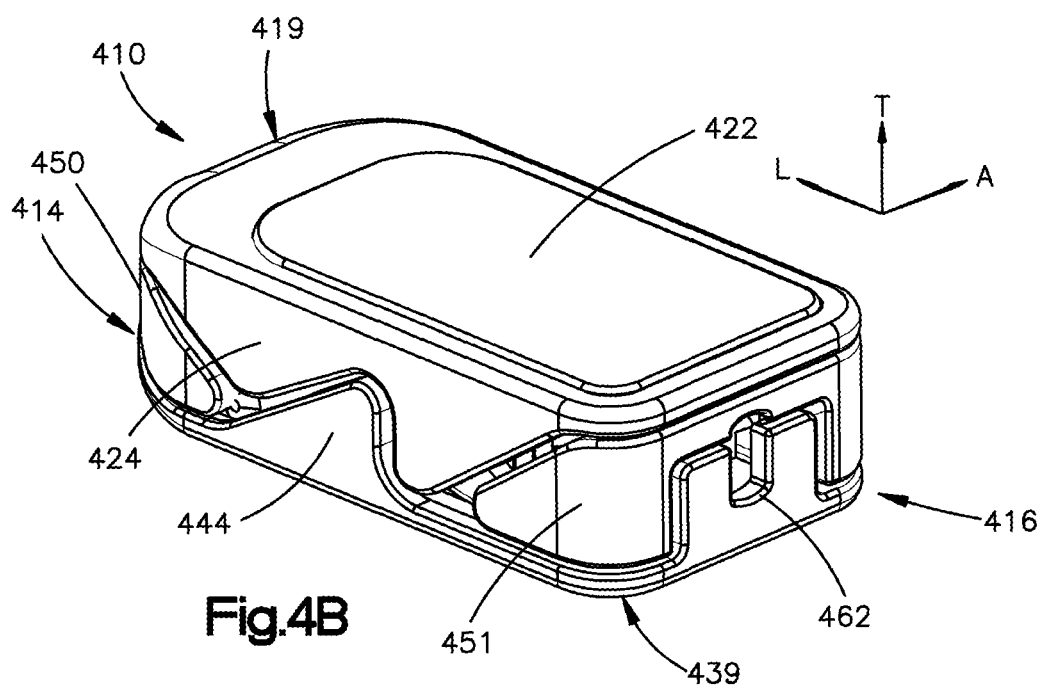
FIG. 4B is another perspective view of the intervertebral cage illustrated in FIG. 4A.
Figure 4G:
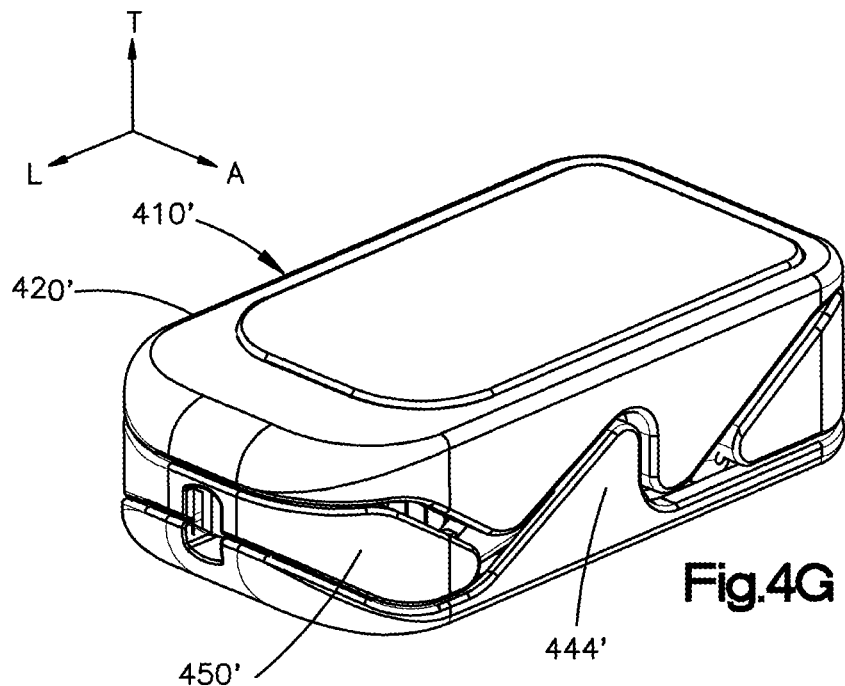
FIG. 4G is a perspective view of an intervertebral cage constructed in accordance with another example, configured for lateral lumbar interbody fusion (LLIF)
Figure 4H:
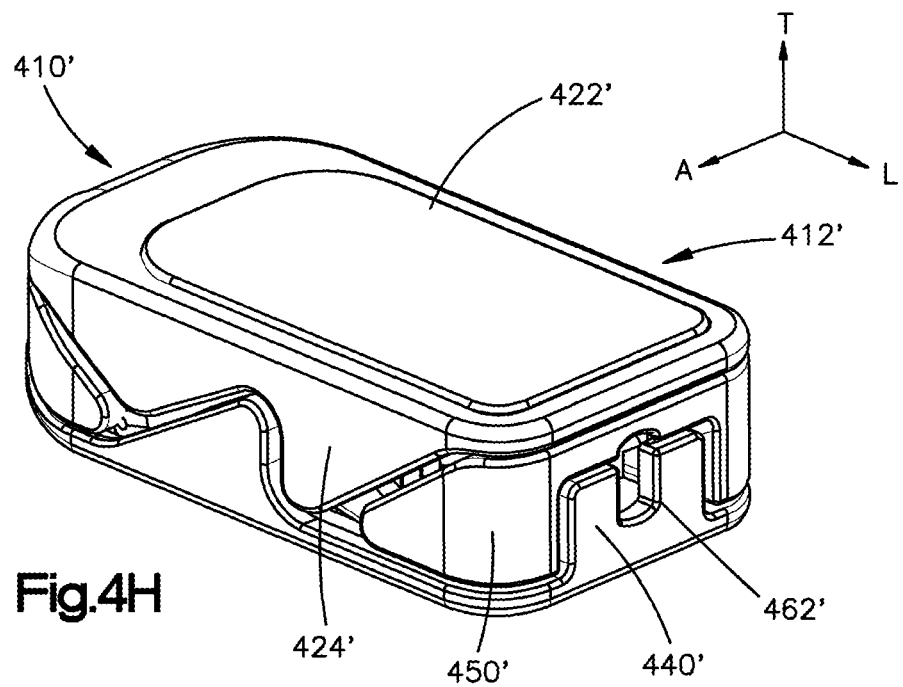
FIG. 4H is another perspective view of the intervertebral cage illustrated in FIG. 4G.
Figure 4L:
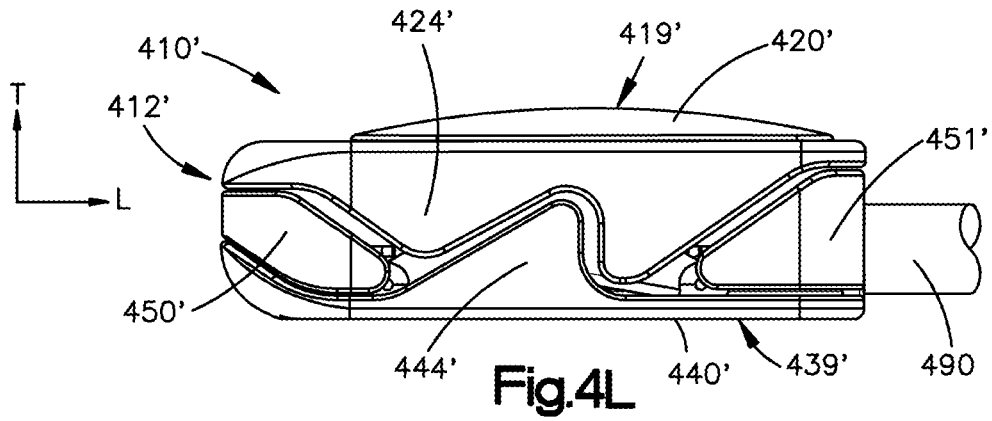
FIG. 4L is a sectional side elevation view of the intervertebral cage illustrated in FIG. 4I, shown attached to an insertion instrument.
Figure 4M:
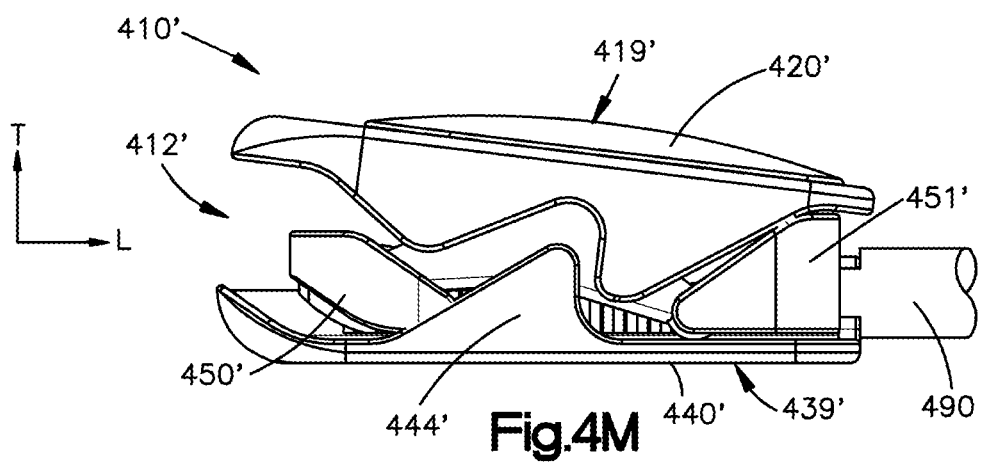
FIG. 4M is a sectional side elevation view of the intervertebral cage illustrated in FIG. 4J, shown attached to an insertion instrument.
Figure 4N:
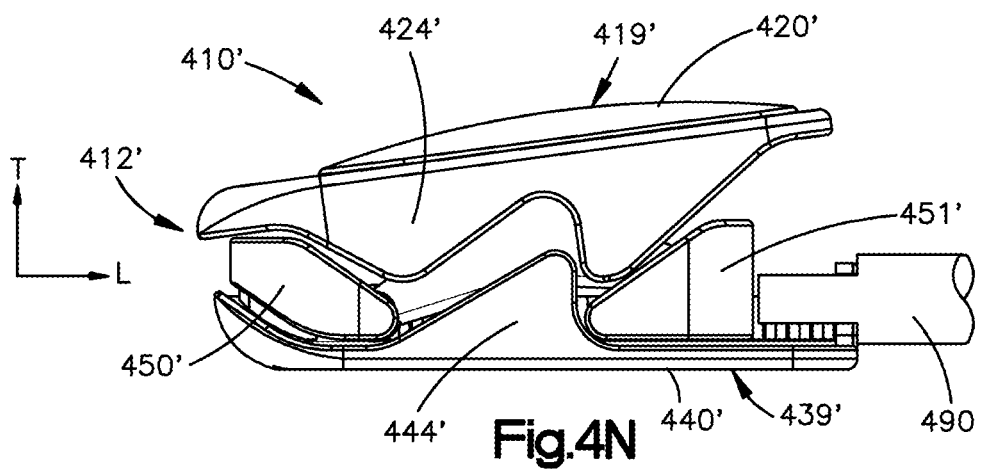
FIG. 4N is a sectional side elevation view of the intervertebral cage illustrated in FIG. 4K, shown attached to an insertion instrument.

FIGS. 4A to 4N illustrate even still more examples of expandable and angularly adjustable intervertebral cages 410, 410' of the present disclosure. FIGS. 4A to 4F show an intervertebral cage 410 configured for anterior lumbar interbody fusion (ALIF), while FIGS. 4G to 4N show the same intervertebral cage 410' but configured for lateral lumbar interbody fusion (LLIF). The intervertebral cage 410 of FIGS. 4A to 4F shown includes features of the intervertebral cage 210 described above, such as the internal mechanism for expansion and angular adjustment. As shown, the cage 410 can include a first or leading end 414 and a second or trailing end 416 opposite the leading end 414 along the longitudinal direction L. The cage 410 can include a housing 412 that includes an upper housing portion 419 and a lower housing portion 439. The upper housing portion 419 can include an upper plate 420 and upper sidewalls 424 that extend down from the upper plate 420 along the transverse direction T. The lower housing portion 439 can include a lower plate 440 and lower sidewalls 444 that extend up from the lower plate 440 along the transverse direction T. The intervertebral cage 410 can further include a pair of wedges 450 and 451 that translate on a guide rail 448 located on an inner transverse surface of the lower plate 440, and can move in a manner as described above for intervertebral cage 210. However, the intervertebral cage 410 can further include porous structures 422 on one or both of the upper plate 420 and the lower plate 440 that facilitate cellular activity and bony ingrowth. Thus, the porous structures 422 can define at least a portion of the upper and lower bearing surfaces of the upper and lower plates 420 and 440, respectively.

Referring to FIGS. 4C to 4E, the longitudinal or horizontal movement of the wedges 450 and 451 (independently of one another) effects the expansion in height and the angular adjustment of the plates 420 and 440 relative to one another, as represented by the drawing in FIG. 4F and as described above with respect to the intervertebral cage 210. FIG. 4C shows the intervertebral cage 410 in a first or unexpanded insertion configuration and attached to an insertion and actuation instrument 490. FIG. 4D shows the first wedge 450 longitudinally moved towards the second wedge 451 using the attached instrument 490, causing the cage 410 to expand and also be angularly adjusted. FIG. 4E shows the second wedge 451 longitudinally moved towards the first wedge 450 using the attached instrument 490, causing the cage 410 to expand and also be oppositely angularly adjusted. Thus, it should be appreciated that the independent movement of the wedges 450 and 451 allows the user to adjust the angle of the cage 410 between a first angle whereby the upper plate 420 is sloped toward the lower plate in a first longitudinal direction and a second angle whereby the upper plate 420 is sloped toward the lower plate 440 in a second longitudinal direction that is opposite the first longitudinal direction, as shown schematically in FIG. 4F.

In general, the intervertebral cage 410 of the present disclosure may be configured for anterior lumbar interbody fusion (ALIF). The cage 410 can be dimensioned as desired. In one example, the cage 410 may have dimensions ranging from 34×25; 37×27; 40×29; and 45×32 mm. Thus, the longitudinal length of the cage 410 can range from approximately 34 mm and approximately 45 mm (with approximately 1 mm increments therebetween). The lateral width of the cage 410 can range from approximately 25 mm to approximately 32 mm (with approximately 1 mm increments therebetween). The height of the cage 410 along the transverse direction from the upper bearing surface to the lower bearing surface can range from approximately 8 mm to approximately 20 mm (with approximately 1 mm increments therebetween). The term "approximate" recognizes manufacturing tolerances and other potential variations, and includes plus or minus 10% of the stated number. The angular adjustment may range from and to approximately 0 degrees, approximately 5 degrees, approximately 10 degrees, approximately 15 degrees, and approximately 20 degrees. It is contemplated that the cage 410 may allow a small step adjustment, and be reversible during the procedure. The cage 410 may be printed in one run, with deployment of the wedges 450 being independent and with the use of the dedicated actuator/insertion instrument 490.

FIGS. 4G to 4N illustrate an intervertebral cage 410' that is similar to the intervertebral cage 410 previously described above, but configured for lateral lumbar interbody fusion (LLIF). While the cage 410 can be configured to angulate in the sagittal plane once implanted into the intervertebral disc space, the cage 410' can be configured to angulate in the coronal plane when implanted into the intervertebral disc space. The cage 410' is otherwise the same as cage 410, and therefore share similar features as represented by the same reference number followed by the symbol "'". As shown, the cage 410' may include a housing 412' that, in turn, includes an upper housing portion 419' and a lower housing portion 439'. The upper housing portion 419' includes an upper plate 420' and upper sidewalls 424' that extend down from the upper plate 420' along the transverse direction T. The lower hosing portion 439' includes a lower plate 440' and lower sidewalls 444' that extend up from the lower plate 440' along the transverse direction T. The intervertebral cage 410' can include a pair of wedges 450' and 451' that translate on a guide rail 448' located on the inner transverse surface of the lower plate 440', and move in a manner similar to what was described above for intervertebral cages 210 and 410. The upper housing portion 419' can also have porous structures 422' on the upper plate 420' may also have porous structures 422' that facilitate cellular activity and bony ingrowth. Thus, at least a portion of the upper bearing surface of the upper plate 420' can be defined by the porous structures 422'.

As shown in FIGS. 4I to 4N, the lateral or horizontal movement of the wedges 450' (independently of one another) effects the expansion in height and the angular adjustment of the plates 420', 440' relative to one another. FIGS. 4I and 4L show the intervertebral cage 410' in a first or unexpanded insertion configuration and attached to an insertion/actuation instrument 490. The wedges 450' and 451' of the intervertebral cage 410 can be longitudinally moved towards one another independently in FIGS. 4J and 4M using the attached instrument 490, causing the cage 410' to expand and also be angularly adjusted in the manner described above. The independent movement of the wedges 450' and 451' allows the user to adjust the angle of the cage 410', as shown in FIGS. 4K and 4N.

In general, the intervertebral cage 410' of the present disclosure may be configured for lateral lumbar interbody fusion (LLIF), and in one example, may have a longitudinal dimension ranging from approximately 40 mm to approximately 60 mm, including approximately 40 mm, approximately 45 mm, approximately 50 mm, approximately 55 mm, and approximately 60 mm. The cage 410 can have a lateral dimension that ranges from approximately 22 mm to approximately 26 mm, including approximately 22 mm and approximately 26 mm. The age can have a height that ranges from approximately 8 mm to approximately 16 mm (with approximately 1 mm increments therebetween). The angular adjustment of the cage 410' may range from approximately 0 degrees to approximately 16 degrees, including approximately 0 approximately, approximately 8 degrees, and approximately 16 degrees, as measured by an angle defined by the upper and lower plates 420' and 440'. It is contemplated that the cage 410' may allow a small step adjustment, and be reversible during the procedure. The cage 410' may be printed in one run, with deployment of the wedges 450' being independent and with the use of the dedicated actuator/insertion instrument 490.

FIGS. 5A to 5D illustrate even further still another example of an expandable and angularly adjustable intervertebral cage 510 of the present disclosure which utilizes many of the same features of the examples described above. As shown, the cage 510 can include a housing 512 that includes an upper housing portion 519 and a lower housing portion 539. The upper housing portion 519 can include an upper plate 520 and upper sidewalls 524 that extend down from the upper plate 520. The lower housing portion 539 can include a lower plate 540 and lower sidewalls 544 that extend up from the lower plate 540. The intervertebral cage 510 can further include a pair of first and second wedges 550 and 551 that translate independently of each other on a guide rail 548 located on an inner transverse surface of the lower plate 540. The wedges 550 and 551 can move in the manner described above with respect to the intervertebral cage 210 so as to expand and angularly adjust the intervertebral cage 510 in the manner described above with respect to the cage 210. In addition, the upper and lower plates 520 and 540 may be connected with elastic springs 530 to control the relative movement of the plates 520 and 540 in the manner described above. The springs 530 can be configured geometrically as elastically deformable strips 530, or can be alternatively configured as desired.

Figure 5A:
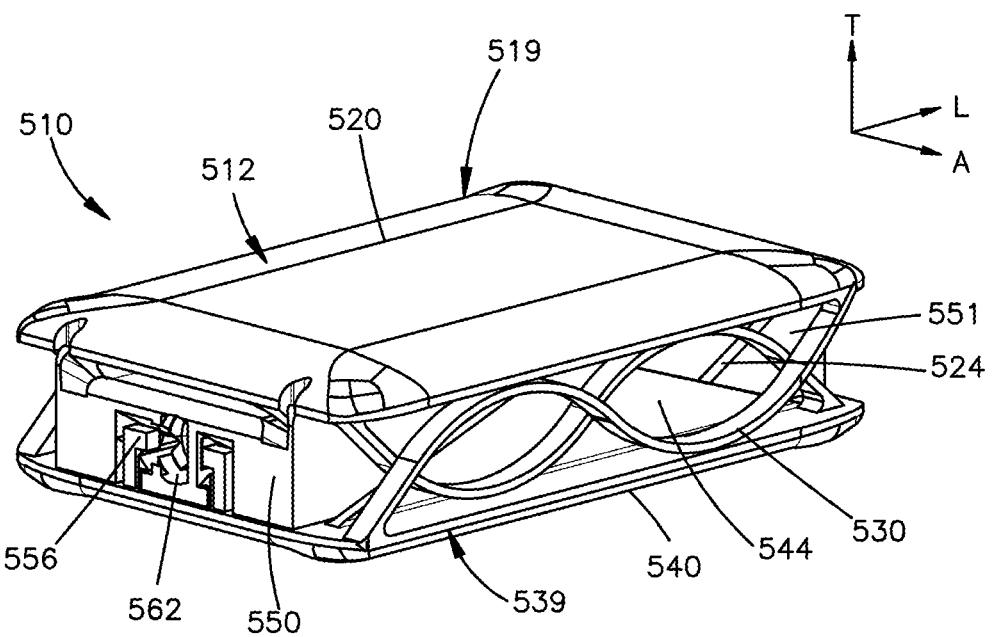
FIG. 5A is a perspective view of the intervertebral cage constructed in accordance with another example.
Figure 5B:
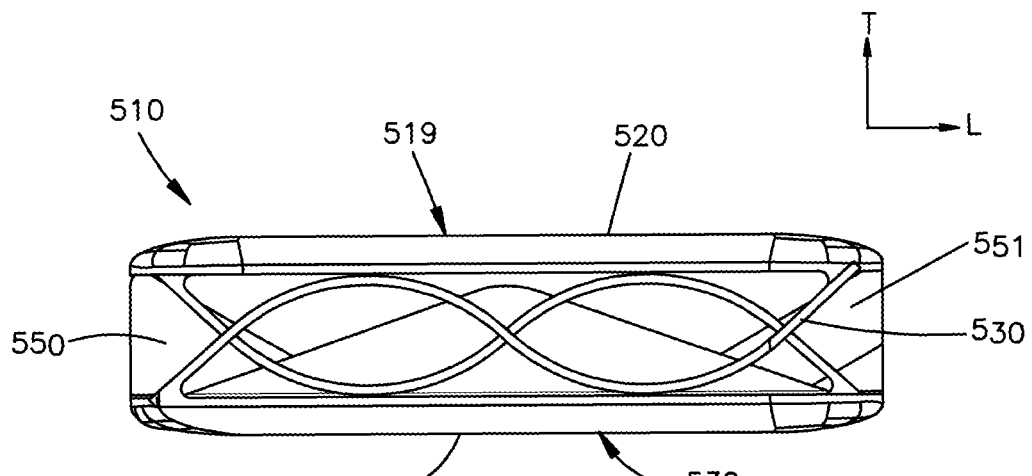
FIG. 5B is a side elevation view of the intervertebral cage illustrated in FIG. 5A, shown in an unexpanded, insertion configuration.
Figure 5C:
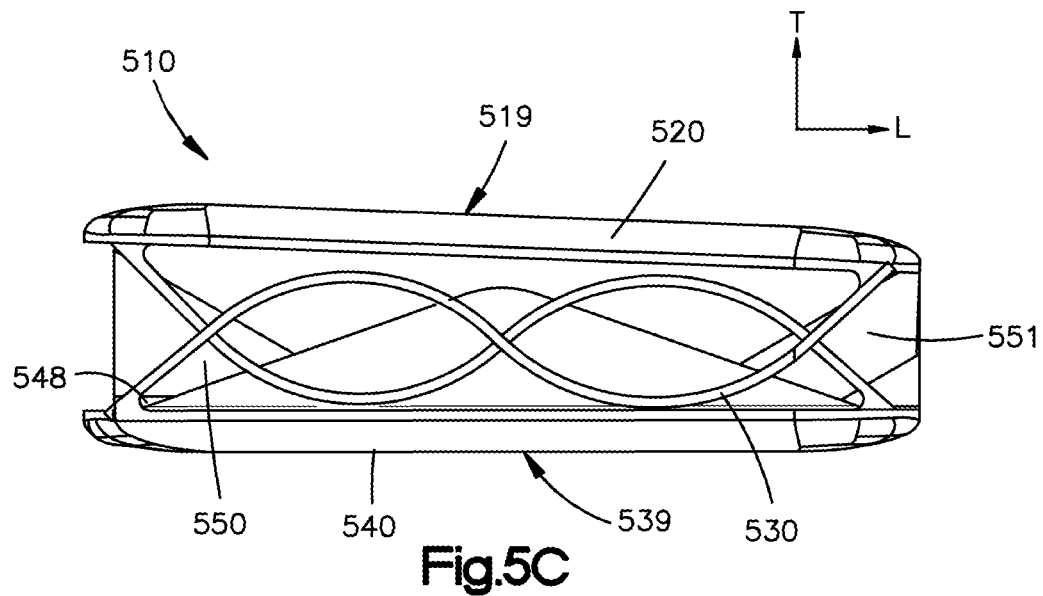
FIG. 5C is a side elevation view of the intervertebral cage illustrated in FIG. 5B, but shown in an expanded and angularly adjusted configuration.
Figure 5D:
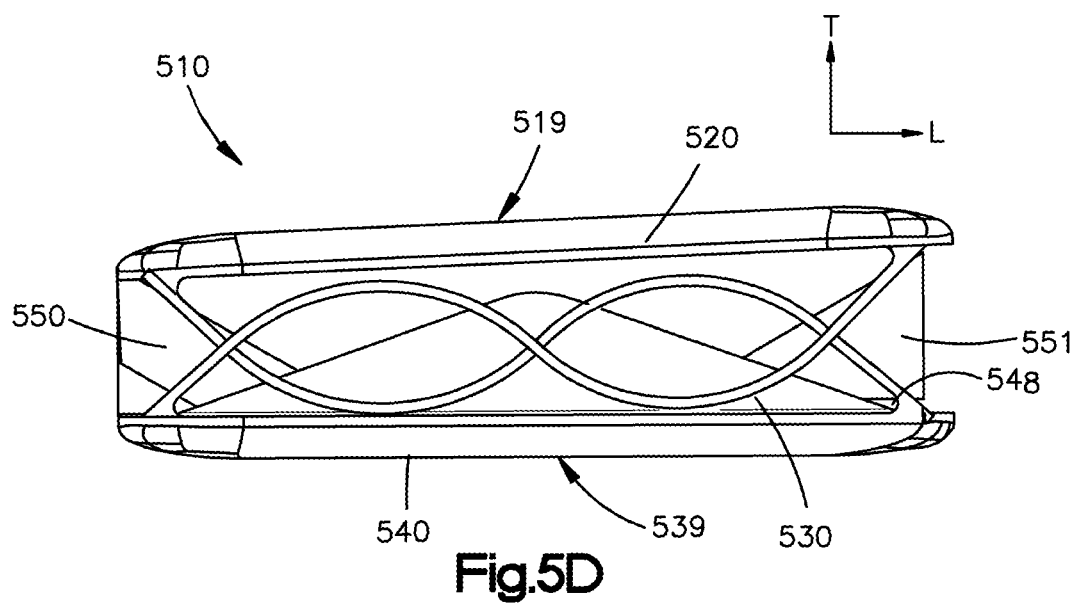
FIG. 5D is another side elevation view of the intervertebral cage illustrated in FIG. 5B, shown in an expanded and angularly adjusted configuration.

As shown in FIG. 5B, when the intervertebral cage 510 is in its compressed, insertion configuration, the wedges 550 and 551 are in their initial configuration. As shown in FIG. 5C movement of the first wedge 550 toward the second wedge 551 along the guide rail 548 causes the upper plate 520 to move away from the lower plate 540 along the transverse direction (expansion), and further causes the first portion of the upper plate 520 to move relative to the second portion of the upper plate 520 away from the lower plate 540 along the transverse direction, thereby angularly adjusting the intervertebral cage 510. As shown in FIG. 5D, movement of the second wedge 551 toward the first wedge 550 along the guide rail 548 causes the upper plate 520 to move away from the lower plate 540 along the transverse direction T (expansion), and further causes the second portion of the upper plate 520 to move relative to the first portion of the upper plate 520 away from the lower plate 540 along the transverse direction, thereby angularly adjusting the intervertebral cage 510. Subsequent movement of the other of the first and second wedges 550 and 551 can return the cage 210 to its first relative angular orientation.

The elastic springs 530 can apply a force against the plates 520 and 540 that resists but allows movement of the upper plate 520 relative to the lower plate 540. The springs 530 can be configured such that free ends of the spring 530 connect the upper plate 520 to the lower plate 540, with no free ends of the spring 530 that are loose and unattached. For instance, one end of the spring 530 can attach to the lower plate 540, and the other end of the spring 530 can attach to the upper plate 520. The intervertebral cage 510 may be particularly advantageous when 3D printed in one run in a metal such as a titanium.

FIGS. 6A to 6F illustrate yet still another example of an expandable and angularly adjustable intervertebral cage 610 of the present disclosure which utilizes many of the same features of the example described above. As shown, the cage 610 can include a housing 612 that, in turn, includes an upper housing portion 619 and a lower housing portion 639. The upper housing portion 619 can include an upper plate 620 and upper sidewalls 624 that extend down from the upper plate 620 along the transverse direction T. The lower housing portion 639 can include a lower plate 640 and lower sidewalls 644 that extend up from the lower plate 640 along the transverse direction T. The intervertebral cage 610 can further include a pair of wedges 650 and 651 that translate on a guide rail 648 located on an inner transverse surface of the lower plate 640, and can move in a manner as described above for intervertebral cage 210. However, as an alternative or in addition to including spring members configured as elastically deformable strips, the cage 610 can include an alternative spring member 630 that resists but allows movement of the cage 610. For instance, in one example, the cage 610 an include the spring 630 configured as a resilient lattice structure 631. The lattice structure 631 can be configured as a honeycomb-like screen 630. The spring member 630 can further define sides of the intervertebral cage 610 that extend from the upper plate 620 to the lower plate 640 and are spaced from each other along the lateral direction A.

Figure 6C:
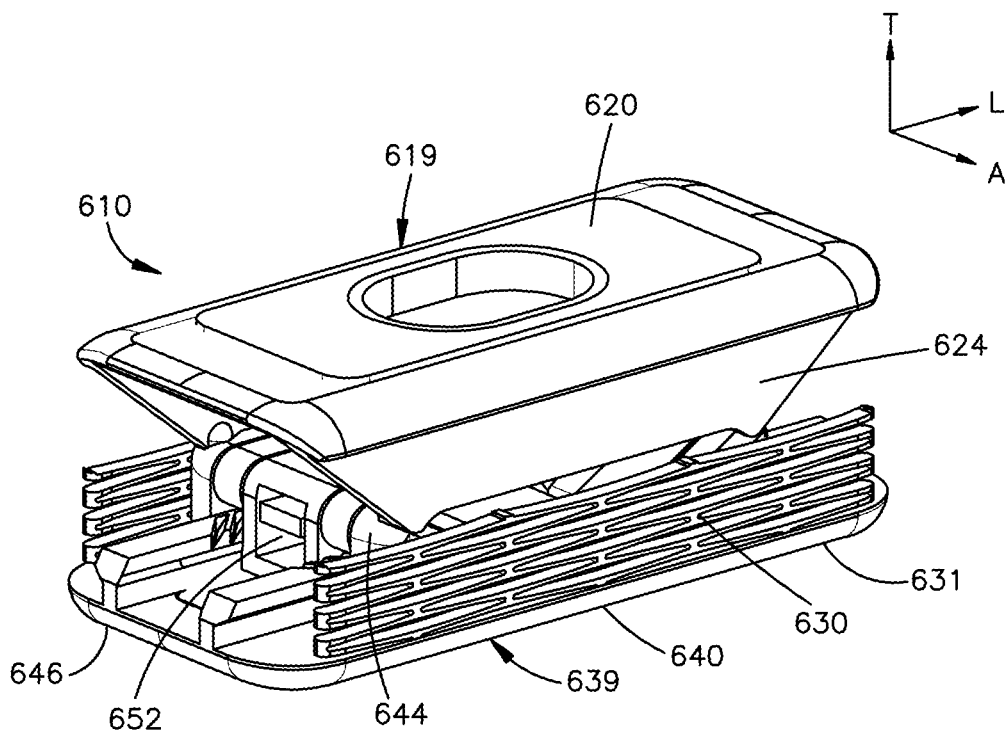
FIG. 6C is a perspective view of the intervertebral cage illustrated in FIG. 6A shown in an expanded configuration.
Figure 6D:
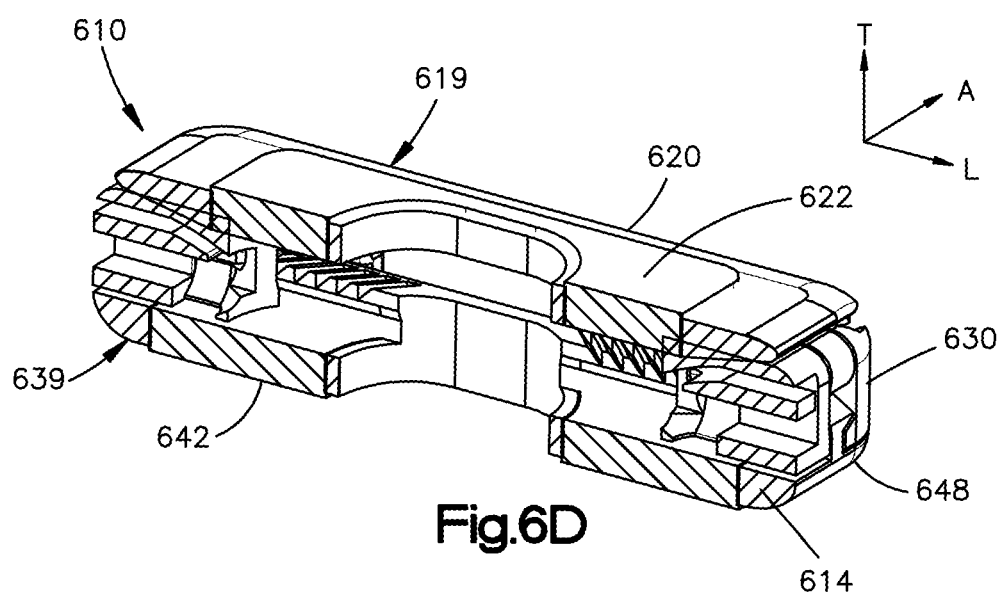
FIG. 6D is a sectional perspective view of the intervertebral cage illustrated in FIG. 6A.
Figure 6E:
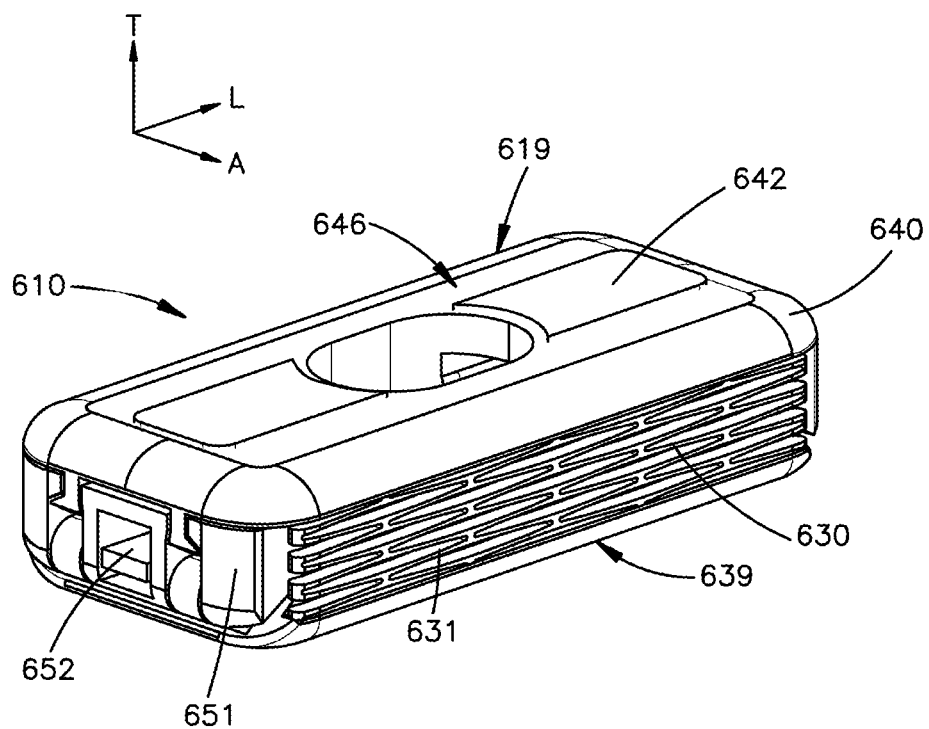
FIG. 6E is a bottom view of the intervertebral cage of FIG. 6A.

The housing 612 can include a pair of wedges 650 and 651 that translate on a guide rail 648 located on a transverse inner surface of the lower plate 640, and move in a manner as described above with respect to the intervertebral cage 210. One or both of the upper plate 620 and the lower plate 640 can include a porous structure as described above with respect to cage 410. For instance, the upper plate 620 can include a porous structure 622 that at least partially define the upper bearing surface. Further, the lower housing portion 639 can include a porous structure 642 that defines the lower bearing, as shown in FIGS. 6D and 6E. Further, one or both of the upper and lower plates 620 and 640 can include teeth 646 configured to grip the respective vertebral endplate. One or both of the wedges 650 and 651 can define an instrument-engagement member that is configured to couple to an actuator that, in turn, is configured to move one or both of the wedges 650 and 651 to expand and/or angulate the intervertebral cage 610. In one example, the instrument-engagement member can be configured as an instrument-engaging opening 652 that is configured to receive an actuator and insertion instrument 690, as shown in FIG. 6B. The actuator and insertion instrument 690 can be configured to insert the cage 610 into the intervertebral space, and can further actuate the cage 610 from its first or insertion configuration to its second or expanded configuration in the manner described above. Further, the instrument 690 can cause the cage 610 to angulate in the manner described above. In particular, the actuation of each of the wedges 650 and 610 for translation towards the other of the wedges 650 and 651 can be achieved in the manner previously described above.

Figure 6G:
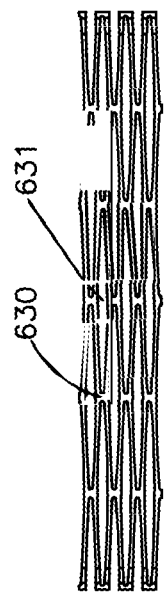
FIG. 6G is a sectional side elevation view of a lattice structure of the intervertebral cage when the cage is in the initial or insertion configuration illustrated in FIG. 6F.
Figure 6I:
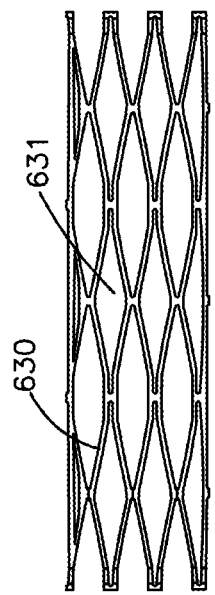
FIG. 6I is a sectional side elevation view of a lattice structure of the intervertebral cage when the cage is in the expanded configuration illustrated in FIG. 6H.
Figure 6K:
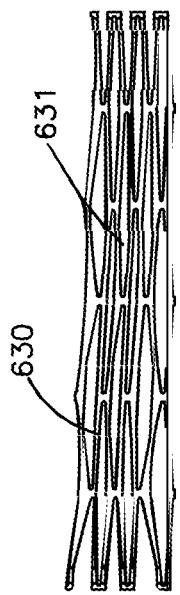
FIG. 6K is a sectional side elevation view of a lattice structure of the intervertebral cage when the cage is in the angularly adjusted configuration illustrated in FIG. 6J.
Figure 6F:
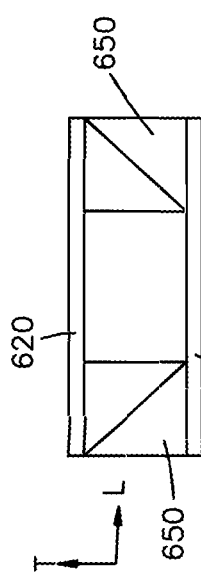
FIG. 6F is a schematic side elevation view of the intervertebral cage illustrated in FIG. 6A, shown in the initial or insertion configuration.
Figure 6H:
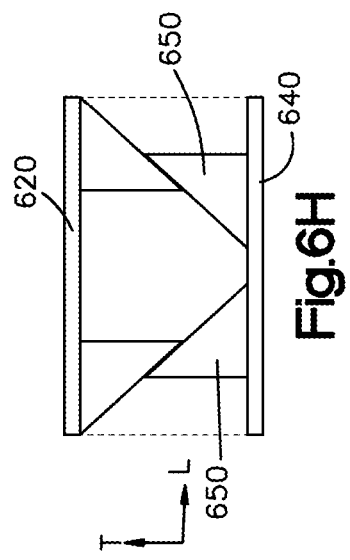
FIG. 6H is a schematic side elevation view of the intervertebral cage illustrated in FIG. 6A, shown in an expanded configuration.
Figure 6J:
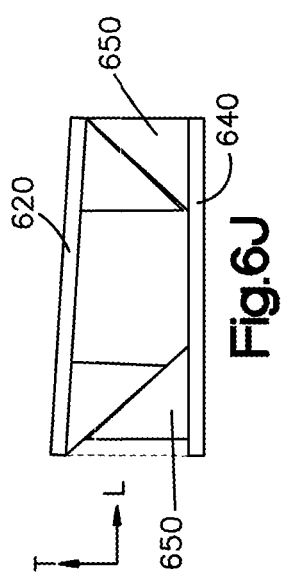
FIG. 6J is a schematic side elevation view of the intervertebral cage illustrated in FIG. 6A, shown in an angularly adjusted configuration.

It is contemplated that the present embodiment may be particularly useful for achieving both distraction and angulation in the coronal plane, using one device. The cage 610 may be effective to restore sagittal balance, while still being less invasive, and due to its ability to be angulated in the coronal plane, is effective for treating degenerative scoliosis or to correct other coronal plane abnormalities. The cage 610 of the present disclosure can achieve these dual goals by providing two independently movable wedges 650 and 651 from the first or insertion configuration illustrated in FIGS. 6F-6G, in which the spring member 630 can be in a relaxed configuration. That is, the lattice structure 631 of the spring 630 can be relaxed and thus not apply a force to either of the upper and lower plates 620 and 640. The wedges 650 and 651 may be moved by the same amount, to distract, as shown in FIGS. 6H-6I. As illustrated in FIGS. 6H and 6I, when the intervertebral cage is in the second or expanded configuration with the second relative angular orientation equal to the first relative angular orientation, the lattice structure 631 of the spring 630 can be placed in tension along the transverse direction T. Thus, the lattice structure 631 applies a compressive force to the upper and lower endplates 620 and 640 along the transverse direction T that biases the upper and lower endplates 620 and 60 toward each other. The wedges 650 and 651 overcome the force as they move the cage 610 to the expanded configuration. Alternatively or additionally, referring now to FIGS. 6J-6K, one of the wedges 650 and 651 may be moved only to effect angulation only, or both wedges 650 and 651 may be moved a disproportionate amount so that there is both distraction and angulation.

When the cage 610 is angulated, one longitudinal end of the lattice structure 631 can be placed in tension greater than the other longitudinal end of the lattice structure 631. The other longitudinal end of the lattice structure 631 can be placed in compression or lesser tension, or can otherwise be neutral. Generally speaking, the amount of height increase or expansion of the cage 610 along the transverse direction T can be dependent on the implant height. In some embodiments, the expansion may be in the range of up to approximately 5 mm. Angulation can be in the range from about 0 degrees up to approximately 16 degrees, including from approximately 0 degrees to approximately 8 degrees.

As mentioned above, the intervertebral cages of the present disclosure are configured to be able to allow insertion through a narrow access path, but are able to be expanded and angularly adjusted so that the cages are capable of adjusting the angle of lordosis of the vertebral segments. By being able to angularly adjust and expand (or distract), the cages allow a very narrow anterior for insertion and a larger anterior after implantation to accommodate and adapt to larger angles of lordosis or kyphosis. Additionally, the cages can effectively restore sagittal balance and alignment of the spine, and can promote fusion to immobilize and stabilize the spinal segment.

With respect to the ability of the expandable cages to promote fusion, many in-vitro and in-vivo studies on bone healing and fusion have shown that porosity can facilitate vascularization, and that the desired infrastructure for promoting new bone growth should have a porous interconnected pore network with surface properties that are optimized for cell attachment, migration, proliferation and differentiation. At the same time, it is believed that cage's ability to provide adequate structural support or mechanical integrity for new cellular activity is another primary factor for achieving clinical success. Regardless of the relative importance of one aspect in comparison to the other, what is clear is that both structural integrity to stabilize, as well as the porous structure to support cellular growth, can assist in proper and sustainable bone regrowth.

The cages described herein can further take advantage of current additive manufacturing techniques that allow for greater customization of the devices by creating a unitary body that may have both solid and porous features in one. In some embodiments as shown, the cages can have a porous structure, and be made with an engineered cellular structure that includes a network of pores, microstructures and nanostructures to facilitate osteosynthesis. For example, the engineered cellular structure can comprise an interconnected network of pores and other micro and nano sized structures that take on a mesh-like appearance. These engineered cellular structures can be provided by etching or blasting to change the surface of the device on the nano level. One type of etching process may utilize, for example, HF acid treatment. These same manufacturing techniques may be employed to provide these cages with an internal imaging marker. For example, these cages can also include internal imaging markers that allow the user to properly align the cage and generally facilitate insertion through visualization during navigation. The imaging marker shows up as a solid body amongst the mesh under x-ray, fluoroscopy or CT scan, for example. The cages described herein can comprise a single marker, or a plurality of markers. These internal imaging markers greatly facilitate the ease and precision of implanting the cages, since it is possible to manufacture the cages with one or more internally embedded markers for improved visualization during navigation and implantation.

Another benefit provided by the implantable devices of the present disclosure is that they are able to be specifically customized to the patient's needs. Customization of the implantable devices is relevant to providing a preferred modulus matching between the implant device and the various qualities and types of bone being treated, such as for example, cortical versus cancellous, apophyseal versus central, and sclerotic versus osteopenic bone, each of which has its own different compression to structural failure data. Likewise, similar data can also be generated for various implant designs, such as for example, porous versus solid, trabecular versus non-trabecular, etc. Such data may be cadaveric, or computer finite element generated. Clinical correlation with, for example, DEXA data can also allow implantable devices to be designed specifically for use with sclerotic, normal, or osteopenic bone. Thus, the ability to provide customized implantable devices such as the ones provided herein allow the matching of the Elastic Modulus of Complex Structures (EMOCS), which enable implantable devices to be engineered to minimize mismatch, mitigate subsidence and optimize healing, thereby providing better clinical outcomes.

A variety of spinal implants may be provided by the present disclosure, including interbody fusion cages for use in either the cervical or lumbar region of the spine. Further, it is contemplated that the principles of this disclosure may be utilized in a cervical interbody fusion (CIF) device, a transforaminal lumbar interbody fusion (TLIF) device, anterior lumbar interbody fusion (ALIF) cages, lateral lumbar interbody fusion (LLIF) cages, posterior lumbar interbody fusion (PLIF) cages, and oblique lumbar interbody fusion (OLIF) cages.

It should be appreciated that the illustrations and discussions of the embodiments shown in the figures are for exemplary purposes only, and should not be construed limiting the disclosure. One skilled in the art will appreciate that the present disclosure contemplates various embodiments. Additionally, it should be understood that the concepts described above with the above-described embodiments may be employed alone or in combination with any of the other embodiments described above. It should be further appreciated that the various alternative embodiments described above with respect to one illustrated embodiment can apply to all embodiments as described herein, unless otherwise indicated.

What is claimed is:

1. An expandable intervertebral cage, comprising:
    a proximal end and a distal end opposite each other along a longitudinal direction;
    an upper housing portion having an upper plate that defines an upper bearing surface configured to face an endplate of a first vertebral body;
    a lower housing portion having a lower plate that defines a lower bearing surface configured to face an endplate of a second vertebral body, wherein a respective entirety of the upper housing portion, including free proximal and distal ends of the upper housing portion, is movable away from the lower housing portion along a vertical direction that is perpendicular to the longitudinal direction;
    first and second guide rails that are spaced from each other along a lateral direction that is perpendicular to each of the longitudinal direction and the vertical direction, each of the guide rails including a plurality of teeth that are arranged in first and second columns defined by the first and second guide rails, respectively, wherein the teeth of the first column are separate from the teeth of the second column;
    an expansion and angular adjustment mechanism disposed between the upper and lower plates, and configured to effect height and angular adjustment of the intervertebral cage, the expansion and angular adjustment mechanism comprising a wedge having an upper engagement surface configured to be urged along the longitudinal direction along the guide rails so as to move the upper housing portion away from the lower housing portion along the vertical direction, such that the upper housing portion angulates relative to the lower housing portion;
    wherein the wedge is configured to interlock with the teeth of the first and second guide rails, and
    wherein each of the guide rails is received by a channel that extends through the wedge.

2. The expandable intervertebral cage of claim 1, wherein the guide rails are supported by the lower endplate.

3. The expandable intervertebral cage of claim 1, wherein the wedge is the only wedge that causes the cage to expand.

4. The expandable intervertebral cage of claim 1, wherein the wedge is urged in a first direction along the longitudinal direction along the guide rails so as to move the upper housing portion away from the lower housing portion along the vertical direction, and the wedge comprises a finger that is configured to interlock with the teeth of one of the guide rails to prevent the wedge from moving in a second direction along the longitudinal direction that is opposite the first direction.

5. The expandable intervertebral cage of claim 4, wherein the finger that is configured to interlock with the teeth of the one of the guide rails prevents the wedge from moving in each of the first direction and the second direction.

6. The expandable intervertebral cage of claim 4, wherein the upper plate angulates relative to the lower plate as the upper plate expands in response to movement of the wedge in the first direction.

7. The expandable intervertebral cage of claim 4, wherein the upper plate extends toward the lower plate in a second direction along the longitudinal direction opposite the first direction after the upper housing has moved away from the lower housing.

8. The expandable intervertebral cage of claim 1, wherein the teeth of one of the first column face away from the teeth of the second column.

9. The expandable intervertebral cage of claim 1, wherein the wedge is disposed between the upper housing portion and the lower housing portion.

10. The expandable intervertebral cage of claim 1, wherein the upper bearing surface is configured for placement against the endplate of the first vertebral body, and the lower bearing surface is configured for placement against the endplate of the second vertebral body.

11. The expandable intervertebral cage of claim 10, wherein the upper plate portion has upper side walls that extend out from the upper pate, and the lower plate portion has lower sidewalls that extend out from the lower plate.

12. The expandable intervertebral cage of claim 1, wherein the columns are parallel to each other before, during, and after movement of the upper housing portion away from the lower housing portion.

13. A method of implanting an intervertebral cage into an intervertebral disc space, the method comprising the steps of:
  inserting the intervertebral cage into the intervertebral disc space in a distal direction that is oriented along a longitudinal direction such that an upper bearing surface of an upper housing portion of the cage faces an endplate of a first vertebral body and a lower bearing surface of a lower housing portion of the cage faces an endplate of a second vertebral body, wherein the intervertebral cage has a proximal end and a distal end opposite each other along the longitudinal direction;
  urging a wedge to move in a first the distal direction along first and second guide rails such that an upper engagement surface of the wedge causes the upper housing portion of the cage to move away from a lower housing portion of the cage along a vertical direction that is perpendicular to the longitudinal direction, such that the upper housing portion angulates relative to the lower housing portion so that the upper housing portion tapers toward the lower housing portion as the upper housing portion extends toward the distal end; and
  causing the wedge to interlock with first and second columns of teeth defined by the first and second guide rails, respectively, wherein the first and second guide rails extend between the proximal and distal ends along the longitudinal direction, the first and second guide rails are spaced from each other along a lateral direction that is perpendicular to each of the longitudinal direction and the vertical direction, and the teeth of the first column are separate from the teeth of the second column,
  wherein each of the guide rails is received by a channel that extends through the wedge during the pushing step.

14. The method of claim 13, wherein the causing step comprises interlocking a finger of the wedge with the teeth of one of the guide rails to prevent the wedge from moving in a second direction that is oriented along the longitudinal direction and opposite the distal direction.

15. The method of claim 14, wherein the interlocking step prevents the wedge from moving in each of the distal direction and a proximal direction that is opposite the distal direction.

16. The method of claim 13, wherein movement of the upper housing portion away from the lower plate causes the upper plate to angulate relative to the lower housing portion.

17. The method of claim 14, wherein the inserting step comprises inserting the intervertebral cage into the intervertebral disc space in the distal direction and the second direction is defined by a proximal direction that is opposite the distal direction.

* * * * *